US012758106B2

(12) United States Patent
Rantanen et al.

(10) Patent No.: US 12,758,106 B2
(45) Date of Patent: *Oct. 13, 2026

(54) TECHNIQUES FOR DETERMINING BLOOD PRESSURE BASED ON MORPHOLOGICAL FEATURES OF PULSES

(71) Applicant: Oura Health Oy, Oulu (FI)

(72) Inventors: Antti Aleksi Rantanen, Oulu (FI); Juha Pekka Pärkkä, Lempäälä (FI); Heli Tuulia Koskimäki, Oulu (FI); Olli Petteri Heikkinen, Oulu (FI); Jukka Tapani Mäkinen, Oulu (FI); Jussi Petteri Järvelä, Kempele (FI); Hannu Hermanni Koivisto, Oulu (FI); Pauli Juhani Ohukainen, Oulu (FI); Juha-Pekka Syrjälä, Oulu (FI)

(73) Assignee: Oura Health Oy, Oulu (FI)

( * ) Notice: Subject to any disclaimer, the term of this patent is extended or adjusted under 35 U.S.C. 154(b) by 0 days.

This patent is subject to a terminal disclaimer.

(21) Appl. No.: 18/435,255

(22) Filed: Feb. 7, 2024

(65) Prior Publication Data

US 2024/0315574 A1 Sep. 26, 2024

Related U.S. Application Data

(63) Continuation of application No. 18/189,849, filed on Mar. 24, 2023, now Pat. No. 11,925,441.

(51) Int. Cl.

| | |
|---|---|
| ***A61B 5/021*** | (2006.01) |
| ***A61B 5/00*** | (2006.01) |
| *A61B 5/024* | (2006.01) |

(52) U.S. Cl.

CPC ............ *A61B 5/021* (2013.01); *A61B 5/6802* (2013.01); *A61B 5/742* (2013.01); *A61B 5/7475* (2013.01);

(Continued)

(58) Field of Classification Search

CPC ....... A61B 5/021; A61B 5/6802; A61B 5/742; A61B 5/7475; A61B 5/02438; A61B 2560/0223

See application file for complete search history.

(56) References Cited

U.S. PATENT DOCUMENTS

| | | | |
|---|---|---|---|
| 10,750,960 | B2 | 8/2020 | Miao et al. |
| 10,827,934 | B2 | 11/2020 | Oksala et al. |

(Continued)

FOREIGN PATENT DOCUMENTS

| | | | |
|---|---|---|---|
| CN | 114680819 | A | 7/2022 |
| EP | 3136954 | A2 | 3/2017 |

(Continued)

OTHER PUBLICATIONS

International search Report and written opinion received for PCT application No. PCT/US2023/016430, mailed on Dec. 21, 2023, 14 pages.

(Continued)

*Primary Examiner* — Patricia J Park
(74) *Attorney, Agent, or Firm* — ArentFox Schiff LLP

(57) ABSTRACT

Methods, systems, and devices for determining blood pressure based on morphological features of pulses are described. A system may include a wearable device that uses one or more light emitting components configured to emit light, one or more photodetectors configured to receive light, and a controller that couples the one or more light emitting components to the one or more photodetectors. The wearable device may transmit lights associated with multiple wavelengths, and acquire photoplethysmogram (PPG) data that includes one or more PPG waveforms associated with the respective wavelengths. The system may determine respective sets of morphological features associated with each of the PPG waveforms based on systolic and diastolic peaks corresponding to the heartbeat of the user. The system (Continued)

may determine one or more blood pressure metrics for the user based at least in part on a comparison of the respective sets of morphological features.

18 Claims, 8 Drawing Sheets

(52) U.S. Cl.
CPC ... *A61B 5/02438* (2013.01); *A61B 2560/0223* (2013.01)

(56) References Cited

U.S. PATENT DOCUMENTS

| | | | |
|---|---|---|---|
| 2002/0058876 A1 | 5/2002 | Chen et al. | |
| 2003/0109791 A1 | 6/2003 | Kondo et al. | |
| 2005/0261593 A1 | 11/2005 | Zhang et al. | |
| 2010/0298726 A1* | 11/2010 | Kim | A61B 5/02225 600/493 |
| 2012/0029363 A1 | 2/2012 | Lund | |
| 2012/0179011 A1* | 7/2012 | Moon | A61B 5/28 600/324 |
| 2017/0027459 A1 | 2/2017 | Shimuta | |
| 2017/0143216 A1 | 5/2017 | Oksala et al. | |
| 2017/0181649 A1* | 6/2017 | Carter | A61B 5/02416 |
| 2019/0060568 A1* | 2/2019 | Newberry | A61M 5/1723 |
| 2019/0110758 A1 | 4/2019 | Kang et al. | |
| 2019/0125198 A1 | 5/2019 | Kang et al. | |
| 2019/0286233 A1* | 9/2019 | Newberry | A61B 5/0075 |
| 2020/0146630 A1 | 5/2020 | Joe et al. | |
| 2020/0237317 A1* | 7/2020 | Newberry | A61B 5/1455 |
| 2020/0297220 A1* | 9/2020 | Lu | A61B 5/02141 |
| 2020/0397311 A1 | 12/2020 | Jung et al. | |
| 2020/0405159 A1 | 12/2020 | Archdeacon | |
| 2021/0022639 A1 | 1/2021 | Iwade et al. | |
| 2021/0030367 A1 | 2/2021 | Cho et al. | |
| 2021/0059585 A1 | 3/2021 | Choi et al. | |
| 2021/0153757 A1 | 5/2021 | Jeon et al. | |
| 2023/0055617 A1 | 2/2023 | Lange et al. | |
| 2023/0068620 A1 | 3/2023 | Tadele et al. | |
| 2024/0005432 A1 | 1/2024 | Aman et al. | |
| 2024/0172945 A1* | 5/2024 | Park | A61B 5/7246 |
| 2024/0315575 A1 | 9/2024 | Pärkkä et al. | |
| 2024/0315578 A1 | 9/2024 | Rantanen et al. | |

FOREIGN PATENT DOCUMENTS

| | | |
|---|---|---|
| WO | 98/17172 A2 | 4/1998 |
| WO | 2012/103296 A2 | 8/2012 |
| WO | 2014/089665 A1 | 6/2014 |
| WO | 2017/147609 A1 | 8/2017 |
| WO | 2017/212120 A1 | 12/2017 |
| WO | 2018/013569 A1 | 1/2018 |
| WO | 2020/105841 A1 | 5/2020 |
| WO | 2021/249850 A1 | 12/2021 |
| WO | 2022/115876 A1 | 6/2022 |
| WO | 2022/146881 A1 | 7/2022 |

OTHER PUBLICATIONS

Invitation to Pay Additional Fees received for PCT application No. PCT/US23/016430, mailed on Oct. 30, 2023, 11 pages.

Obata et al., "Noninvative assessment of the effect of position and exercise on pulse arrival to peripheral vascular beds in healthy volunteers", Frontiers in Physiology, 2017, vol. 8, Article 47 (Year: 2017).

International Search Report and Written Opinion received for PCT Patent Application No. PCT/US2023/016432, mailed on Nov. 3, 2023, 9 pages.

Liu et al, "A Preliminary Study on Multi-Wavelength PPG Based Pulse Transit Time Detection for Cuffless Blood Pressure Measurement", 38th Annual International Conference of the IEEE Engineering in Medicine and Biology Society (EMBC), 2016, pp. 615-618.

Notification of material filed by a third party received for Australian Patent Application No. 2023441282, mailed on Jan. 14, 2026, 17 pages.

Office Action received for European Patent Application No. 23718472.6, mailed on Jan. 20, 2026, 5 pages.

Third Party Observation received for German Patent Application No. 112023003389.7, mailed on Jan. 16, 2026, 42 pages (18 pages of English Translation and 24 pages of Original Document).

Action received for European Patent Application No. 23718880.0, mailed on Aug. 12, 2026, 6 pages.

* cited by examiner

TECHNIQUES FOR DETERMINING BLOOD PRESSURE BASED ON MORPHOLOGICAL FEATURES OF PULSES

CROSS REFERENCE

The present Application for Patent is a Continuation of U.S. patent application Ser. No. 18/189,849 by Rantanen et al., entitled "TECHNIQUES FOR DETERMINING BLOOD PRESSURE BASED ON MORPHOLOGICAL FEATURES OF PULSES," FILED Mar. 24, 2023, which is assigned to the assignee hereof and expressly incorporated by reference herein.

FIELD OF TECHNOLOGY

The following relates to wearable devices and data processing, including techniques for determining blood pressure based on morphological features of pulses.

BACKGROUND

Some wearable devices may be configured to collect data from users associated with blood pressure. However, wearable devices may fail to accurately indicate a blood pressure of a user. That is, a wearable device may fail to accurately perform blood pressure measurements due to signal processing limitations and adequate techniques that allow the hardware of the wearable device to indicate the blood pressure of the user. In some aspects, users may acquire blood pressure measurements in a clinical setting (e.g., a doctor's appointment) with a blood pressure device (e.g., a sphygmomanometer, a blood pressure cuff, a blood pressure monitor). However, the size and shape of the blood pressure device may be inconvenient for everyday use, and in some cases, users may not have access to the blood pressure device to acquire blood pressure measurements consistently. As a result, users may be unaware of specific conditions or diseases associated with high or low blood pressure measurements if blood pressure measurements are infrequently measured for the user.

DETAILED DESCRIPTION

Figure 1:
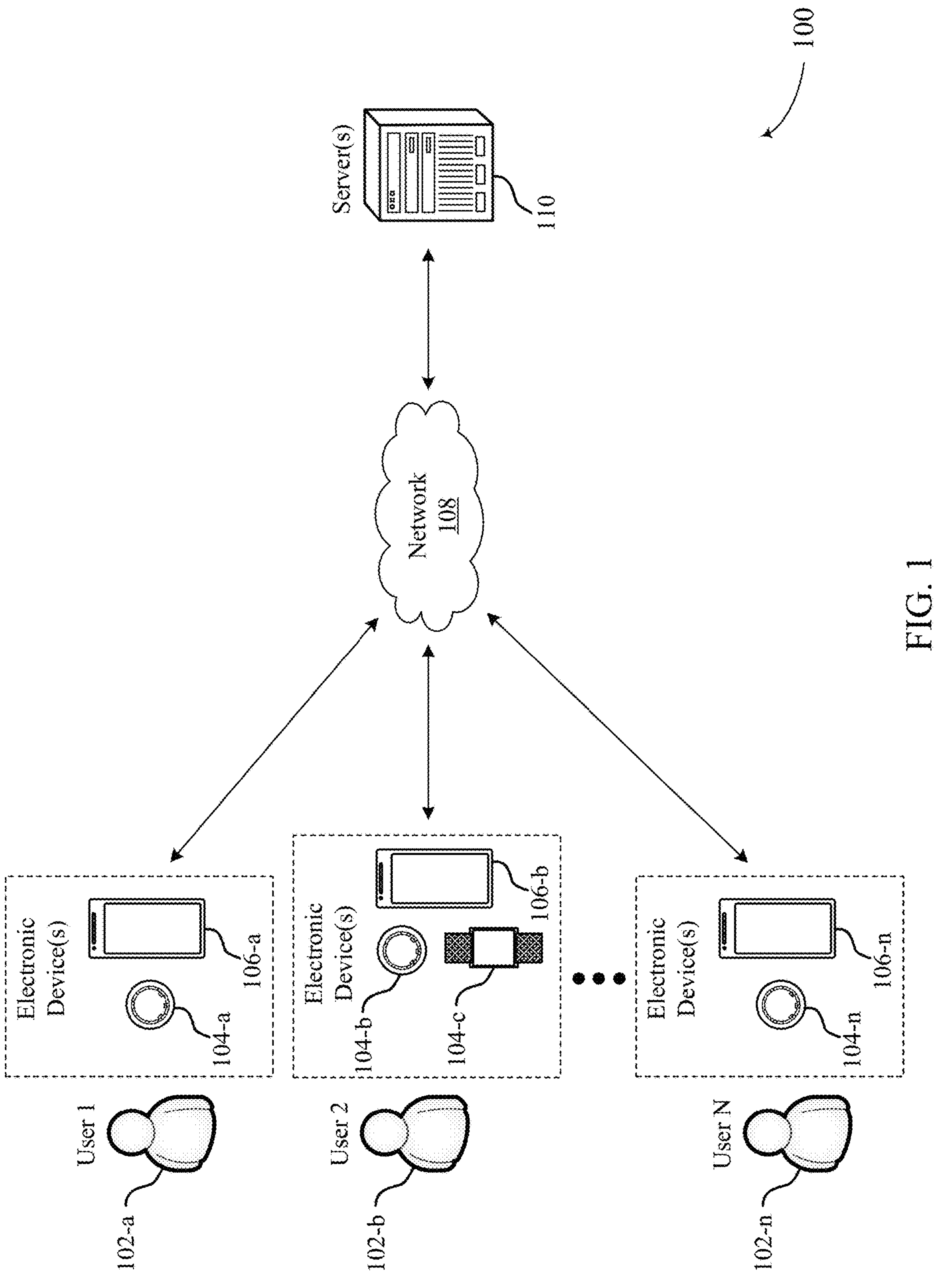
FIG. 1 illustrates an example of a system that supports techniques for determining blood pressure based on morphological features of pulses in accordance with aspects of the present disclosure.

Traditionally, blood pressure has only been able to be measured in a clinical setting, resulting in users only having their blood pressure measured on the few occasions a year that they go into their doctor's office. At-home blood pressure devices have enabled users to measure their blood pressure at home. However, traditional blood pressure devices rely on bulky arm cuffs that are not comfortable (or feasible) to wear consistently.

Some wearable devices have attempted to use light-based measurements to perform blood pressure measurements. However, wearable devices that have attempted to utilize light to acquire physiological data necessary for determining blood pressure may be unable to perform blood pressure measurements due to signal processing limitations. In addition, a lack of information about the relationship between blood pressure and features of photoplethysmogram (PPG) waveforms may prevent some wearable devices from acquiring accurate blood pressure measurements. As such, a system that conveniently measures blood pressure on a consistent (e.g., daily, hourly) basis may be beneficial to the overall health of users.

Accordingly, aspects of the present disclosure are directed to systems that utilize a wearable device (e.g., wearable ring device, watch, necklace, chest-worn wearable device, extremity monitor) to determine one or more blood pressure metrics (e.g., measurements) of the user. In particular, the systems described herein may enable wearable devices to determine blood pressure based on morphological features of pulses (e.g., heartbeat pulses) of the user.

For example, a wearable device may be configured to acquire PPG data from a user, where the PPG data includes one or more PPG waveforms associated with one or more wavelengths of light used to acquire the PPG data. In some examples, PPG pulses within the respective PPG waveforms may display different morphological features based on different projected wavelengths used to acquire the respective PPG pulses (e.g., a first wavelength, a second wavelength, and the like). In such cases, morphological features of the respective PPG waveforms may be used to determine blood pressure metrics for the user. Specifically, the system may acquire PPG data using one or more wavelengths of light, where the PPG data includes one or more PPG waveforms corresponding to the one or more wavelengths of light used to acquire the PPG data. Subsequently, morphological features may be identified within or between the raw PPG waveforms associated with the different wavelengths, and/or within or between one or more derivatives (e.g., a first derivative, a second derivative, and the like) of the raw PPG waveforms.

In some examples, blood pressure may be determined using morphological features that include correlation coefficients between each of the PPG waveforms of different wavelengths, delays between systolic and diastolic peaks of a second derivative of the PPG waveforms of different wavelengths, and differences in systolic peak timings between PPG waveforms of different wavelengths. That is, blood pressure of the user may be determined (e.g., estimated) using the morphological features displayed by multiple PPG waveforms/pulses. As such, the system may use the wearable device placed at relative locations on the user to acquire PPG data, to determine morphological features from the PPG waveforms, and to determine one or more blood pressure metrics of the user.

In some implementations, the system may use the wearable device to determine the one or more blood pressure metrics for the user based on a comparison of morphological features of PPG waveforms. For example, the single wearable device may include one or more light emitting components (e.g., one or more light emitting diodes (LEDs)) configured to emit light associated with a first wavelength and a second wavelength and photodetectors to receive light from the one or more light emitting components. The light emitting components and photodetectors may be coupled to a controller that transmits light associated with one or more wavelengths.

In some aspects, the system may cause light emitting components of a wearable device to transmit first light associated with the first wavelength (e.g., red light) and second light associated with the second wavelength (e.g., infrared (IR) light, green light, etc.) during a time interval that includes a heartbeat of the user. The system may acquire PPG data from the user based on receiving the first light and the second light via the one or more photodetectors. The PPG data may include a first PPG waveform using the first light associated with the first wavelength and a second PPG waveform using the second light associated with the second wavelength. The system may determine a first set of morphological features associated with the first PPG waveform based on a first systolic peak and a first diastolic peak corresponding to the heartbeat for the first PPG waveform. Further, the system may determine a second set of morphological features associated with the second PPG waveform based on a second systolic peak and a second diastolic peak corresponding to the heartbeat for the second PPG waveform. As such, the system may determine one or more blood pressure metrics for the user based on a comparison of the first set of morphological features and the second set of morphological features.

FIG. 1 illustrates an example of a system 100 that supports techniques for determining blood pressure based on morphological features of pulses in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via graphical user interfaces (GUIs)) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for determining blood pressure based on morphological features of PPG waveforms collected from a user 102. As described herein, the system 100 may use a wearable device 104 (e.g., wearable ring device, watch or bracelet, necklace, chest-worn wearable device, headband or strap, extremity monitor) to determine one or more blood pressure metrics (e.g., measurements) of the user 102. That is, the system 100 may utilize the wearable device 104 (which the user 102 may wear on a consistent basis) to determine blood pressure based on morphological features of PPG data (e.g., PPG data/waveforms associated with heartbeat pulses) of the user 102. In some examples, PPG waveforms may display different morphological features based on different projected wavelengths (e.g., a first wavelength, a second wavelength, and the like). In some examples, pulses from a user's heartbeat may be identified from one or more PPG waveforms acquired using one or more wavelengths. Specifically, the system 100 may acquire PPG data using multiple different wavelengths, and morphological features may be identified within or between the raw PPG waveforms/signals of the PPG data corresponding to different wavelengths. Subsequently, the morphological features of the respective PPG waveforms/signals may be evaluated to determine or estimate the user's blood pressure.

In some examples, blood pressure may be determined using morphological features that include correlation coefficients between each of the PPG waveforms of different wavelengths, delays between systolic and diastolic peaks of a second derivative of the PPG waveforms of different wavelengths, and differences in systolic peak timings between PPG waveforms of different wavelengths. That is, blood pressure of the user 102 may be determined (e.g., estimated) using the morphological features displayed by heartbeat pulses captured within the multiple respective PPG waveforms/signals. As such, the system 100 may use the wearable device 104 placed at relative locations on the user 102 to acquire PPG data including multiple PPG signals/waveforms (e.g., PPG waveforms corresponding to different wavelengths), to determine morphological features from the PPG waveforms, and to determine one or more blood pressure metrics of the user 102.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
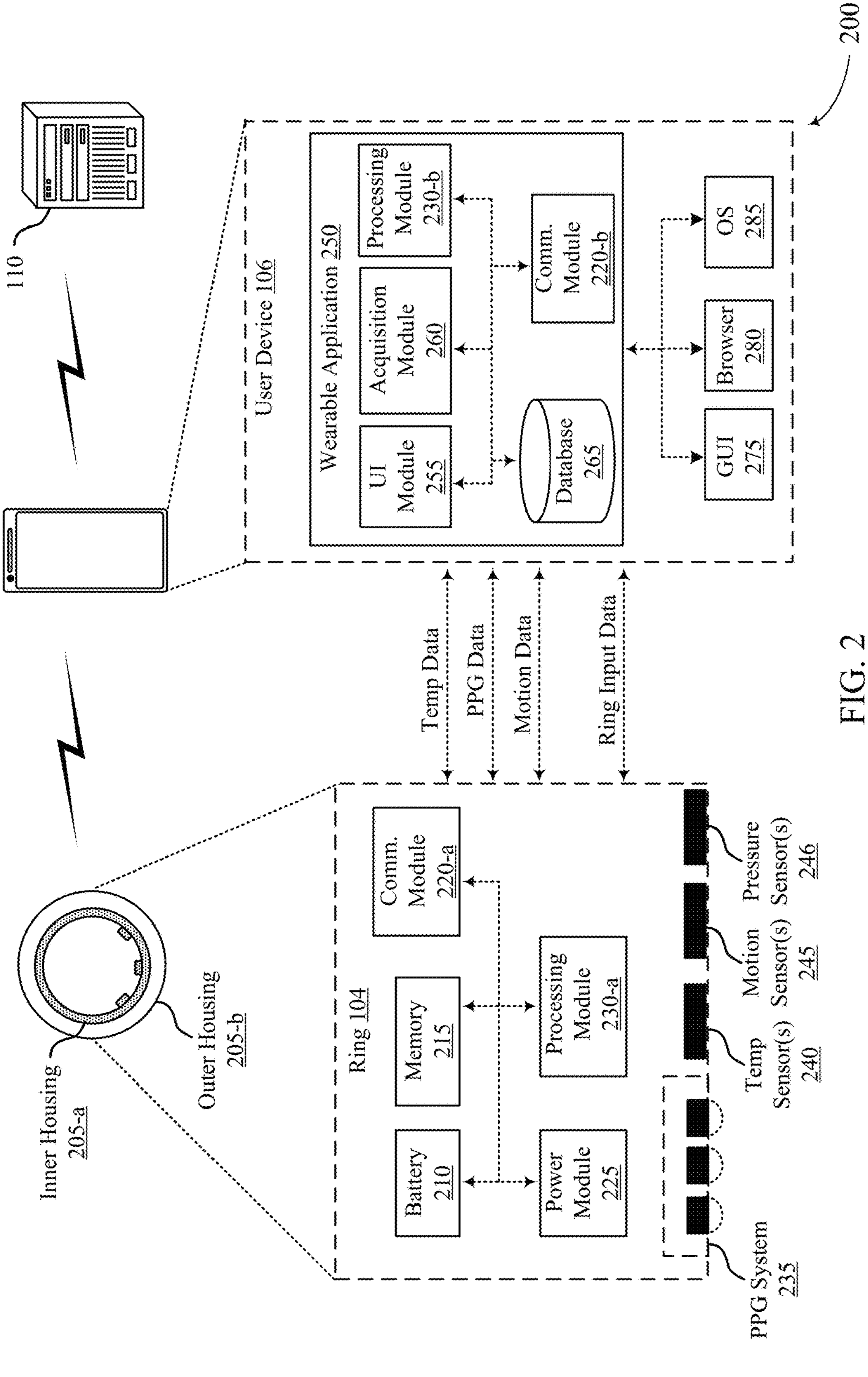
FIG. 2 illustrates an example of a system that supports techniques for determining blood pressure based on morphological features of pulses in accordance with aspects of the present disclosure.

FIG. 2 illustrates an example of a system 200 that supports techniques for determining blood pressure based on morphological features of pulses in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG LEDs. In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module

230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include LEDs. The optical transmitters may transmit light in the IR spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for determining blood pressure based on a relative timing of pulses (e.g., heartbeat pulses). To provide some context for the desire to determine blood pressure, in some examples, one or more users (e.g., individuals) 102 may measure blood pressure regularly in a clinical setting, and therefore users 102 may measure blood pressure infrequently (e.g., once a year, twice a year). In addition, users 102 may not only fail to measure blood pressure but also health measurements related to heart rate, heart rate variability, cardiovascular age, arterial stiffness, AFib, ectopic beats, orthostatic tests, $VO_2$ max, and the like. As such, users 102 may unknowingly fail to take preventative actions based on whether the health measurements indicate positive or negative measurements. That is, if users 102 were aware of one or more health measurements, the users 102 may integrate healthy life choices that include improving nutrition (e.g., eating fruits and vegetables), physical activity, sleep, stress management, or the like. However, as discussed, users 102 rarely attend primary care facilities, where one or more doctors may measure the cardiovascular health of users (e.g., run an electrocardiogram (ECG) test, measure consecutive heartbeat pulses), and therefore users 102 may be unaware of the risk factors, such as an increased risk of heart attack, stroke, heart failure, and other complications.

In particular, users 102 affected by cardiovascular health issues may implement lifestyle choices (e.g., changes) to improve overall cardiovascular health for the long term. For example, users 102 monitoring cardiovascular health may be concerned about risk factors of heart disease and/or stroke and may refrain from an unhealthy diet (e.g., a high salt intake), a lack of physical inactivity, tobacco use, alcohol, or the like. The user 102 may refrain from these actions to avoid an increase in blood pressure, an increase in blood glucose, or an increase in blood lipids that may lead to the user 102 becoming overweight and/or obese. In some examples, users 102 may be concerned about one or more cardiovascular health measurements, such as cardiovascular age, otherwise known as heart age and vascular age. Specifically, heart age is an assessment of well-known risk factors for heart disease (e.g., age, sex, blood pressure, cholesterol) to estimate a user's 102 risk of a heart attack or stroke compared to a defined healthy range. In some cases, when the heart age exceeds the current age of a user 102, the user 102 may be at modifiable risk for developing heart disease.

In other examples, users 102 may be concerned about vascular age, where a vascular age test provides a measurement of the apparent age of users' 102 arteries, compared to healthy users 102. In some instances, the user 102 may display a vascular age that exceeds the user's 102 chronological age and that the user 102 may be at risk for developing a cardiovascular disease (CVD). As such, affected users 102 may implement lifestyle changes such as increasing aerobic exercise, reducing calories, reducing sodium, including flavonoids in the diet, and other healthy dietary patterns to reduce arterial stiffness and blood pressure to reduce vascular aging. In some aspects, the tests that produce cardiovascular age measurements may compare one user's 102 data against multiple users 102. That is, the tests may compare the user's 102 pulse waveform to typical pulse waveforms across different age groups.

In some aspects, cardiovascular health measurements may utilize blood pressure measurements to accurately predict the user's 102 health and wellbeing. That is, blood pressure may indicate binary information that includes a systolic blood pressure measured from one or more arteries when the user's 102 heart beats and diastolic blood pressure measured from one or more arteries when the user's 102 is in between heart beats. In some examples, a classification of blood pressure may include either a normal blood pressure or a high blood pressure. For users 102, a normal blood pressure may indicate a systolic blood pressure of less than 130 millimeters of mercury (mmHg) and a diastolic blood pressure of less than 80 mmHg. Alternatively, a high blood pressure may indicate a systolic blood pressure greater than 130 mmHg and a diastolic blood pressure greater than 80 mmHg.

In some aspects, blood pressure measurements may indicate the pressure of circulating blood against the walls of blood vessels. In some cases, the blood pressure may result from the heart of the user 102 pumping blood through the circulatory system. That is, the heart pumps blood in the form of pulses (e.g., beats), where each pulse has a morphology (e.g., morphological features that describe the size/shape of pulses). Further, each pulse may indicate a different morphology (e.g., size and shape) that corresponds to blood pressure (e.g., high or low). For example, pulses acquired in different methods, such as PPG pulses and arterial blood pressure (ABP) pulses, may indicate different systolic peaks, diastolic peaks, dicrotic notches, pulse widths, slopes of pulses, inflection points, and the like.

In some examples, a comparison of pulses may illustrate differences as a result of PPG pulses acquiring signals non-invasively (e.g., a finger clip device) and ABP pulses acquiring signals invasively (e.g., inserted via a needle directly to a vein of the user). Further, the PPG pulses and ABP pulses may be compared on a graph over time to determine an in-phase analysis. That is, a morphology correlation (e.g., r) may be determined between the PPG and ABP waveforms to accurately determine whether the user falls under a specific blood pressure category, such as normotensive (e.g., normal blood pressure), prehypertensive (e.g., at risk for high blood pressure), or hypertensive (e.g., high blood pressure). As such, for a system to measure blood pressure accordingly, the system may utilize multiple pulses to properly indicate corresponding blood pressure categories of users 102 and determine whether users 102 are at risk for specific blood pressure conditions or diseases.

In some examples, the pulses may be monitored via a spot check, where a binary classification may indicate if the pulse exhibits a normal value or a high value. In other cases, the pulses may be evaluated against a blood pressure trend (e.g., a blood pressure trendline). That is, the pulses may be compared to typical blood pressure trends for the user expressed at different times of the day. In some cases, the pulses may be acquired over a term period (e.g., weekly, monthly, yearly). As such, blood pressure over some amount of time may compare blood pressure of the user that may include the sum of nocturnal, continuous blood pressure. In such instances, constant monitoring (e.g., chronic exposure) of blood pressure may be a key indicator (e.g., determinant) of cardiovascular risk. That is, the area under the curve of blood pressure, in other words the cumulative cardiovascular risk, may be calculated by time multiplied by continuous blood pressure (e.g., area under the curve=time*continuous blood pressure). In some examples, pulses may be compared to typical blood pressure trends at night to determine if a user has nocturnal hypertension based on a dipping of pulses. For the user, a normal, nocturnal blood pressure trend may indicate a blood pressure dipping about 10% to 15% less than typical daytime pulses. However, detecting blood pressure changes (e.g., blood pressure changes based on absolute values and additional values) greater than 15% may indicate a warning that the user has an elevated sodium level, a salt sensitivity, chronic kidney disease (CKD), congestive heart failure (CHF), diabetes, a structural vascular disease, insomnia, or the like. In addition, the U.S. Food and Drug Administration (FDA) permits monitoring pulses via spot checks or blood pressure trends to detect blood pressure of users, and therefore techniques that support these methods would be beneficial to integrate to users outside of a hospital setting.

In some aspects, one or more health care workers (e.g., nurses, doctors) may use a blood pressure device (e.g., a sphygmomanometer, a blood pressure cuff, a blood pressure monitor) that overlooks one or more pulses and determines blood pressure metrics for each user 102. In some examples, the user 102 may use an at home blood pressure device to acquire blood pressure metrics outside a clinical setting. However, the blood pressure device may use one or more arm cuffs that may be uncomfortable for the user to wear consistently. That is, one or more solutions that conveniently measure blood pressure on an everyday basis may enable the user 102 to monitor health issues. However, conventional wearable devices 104 have been unable to perform blood pressure measurements due to signal processing limitations and a lack of information about the relationship between blood pressure and features of PPG waveforms. Thus, methods and/or techniques for conveniently measuring blood pressure on a consistent basis may be desired but yet to be implemented.

Accordingly, aspects of the system 200 may support techniques for determining blood pressure based on morphological features of heartbeat pulses of the user 102. As described herein, the system 200 may use a wearable device 104 (e.g., wearable ring device, watch, necklace, chest-worn wearable device, extremity monitor) to determine one or more blood pressure metrics (e.g., measurements) of the user 102. Further, the wearable device 104 may include one or more light emitting components (e.g., one or more LEDs) configured to emit light associated with a first wavelength and a second wavelength and one or more photodetectors to receive light from the one or more light emitting components. The light emitting components and photodetectors may be coupled to a controller that causes the light emitting components to transmit light associated with one or more wavelengths. That is, the system 200 may enable the wearable device 104 that users 102 wear on a consistent basis to determine blood pressure based on morphological features of pulses (e.g., heartbeat pulses) of the user 102.

In some implementations, the system 200 may determine blood pressure metrics for the user 102 that uses the PPG system 235. That is, the PPG system 235 may include one or more light emitting components (e.g., LEDs) and photodetectors near the surface of the skin to measure the volumetric variations of blood flow of the user 102. In some examples, a triple LED (e.g., red, green, and IR) PPG system 235 may enable the wearable devices 104 to propagate multiple light waves into the tissue of the user 102 based on the specified wavelength of light to acquire physiological data. In some examples, physiological data may include PPG data, acceleration data, pressure data, and the like. That is, the PPG system 235 may enable the system 200 to utilize different components to acquire PPG data.

Additionally, or alternatively, physiological data acquired by the wearable device 104 may include acceleration data (e.g., movement/motion data) associated with the user 102. In some cases, the wearable devices 104 may acquire acceleration data from the one or more motion sensors 245. For example, the wearable device 104 may use the motion sensors 245 to determine the heart rate of the user 102 when the user 102 is in motion (e.g., exercising). That is, the system 200 may use acceleration data to indicate how motion affects blood flow and subsequently blood pressure.

In some aspects, the wearable device 104 may utilize the one or more light emitting components to transmit a first light associated with the first wavelength and transmit a second light associated with the second wavelength during a time interval that includes a heartbeat of the user 102. The system 200 may acquire PPG data from the user 102 based on receiving the first light and the second light via the one or more photodetectors. Further, the PPG data may include a first PPG waveform associated with (e.g., acquired using) the first light associated with the first wavelength and a second PPG waveform associated with (e.g., acquired using) the second light associated with the second wavelength. In some examples, the respective PPG waveforms may include or illustrate one or more heartbeat pulses of the user that exhibit different morphological features based on different projected wavelengths (e.g., a first wavelength, a second wavelength, and the like).

As described herein, the system 200 may acquire PPG data that includes the first PPG waveform acquired using the first light and the second PPG waveform acquired using the second light. That is, each of the PPG waveforms/signals acquired using multiple different wavelengths may depict various morphological features. In some examples, the PPG waveforms/signals may be identified as raw PPG waveforms/signals, such as IR PPG waveforms/signals, red PPG waveforms/signals, green PPG waveforms/signals, and the like. The system 200 may acquire multiple raw PPG waveforms/signals received from the PPG data and determine morphological features that may be identified within or between the raw PPG waveforms of the different wavelengths and one or more derivatives (e.g., a first derivative, a second derivative, and the like) of the raw PPG waveforms. That is, the morphological features may allude to one or more blood pressure metrics of the user 102.

Additionally, or alternatively, the system 200 may acquire data via one or more pressure sensors 246 (e.g., piezoelectric pressure sensors, etc.). In some cases, the physiological data may be acquired during a time interval where a pressure between the wearable device 104 and a tissue of the user 102 is changed. That is, the system 200 may include the wearable device 104 with an optical sensor that contacts the skin of the user 102 and the optical sensor may restrict blood circulation at different skin tissue layers as the pressure between the optical sensor (and/or other surfaces of the wearable device 104) and the tissue of the user is changed. As such, the system 200 may determine a correlation between arterial blood pressure and pulse morphology and may account for external pressure when determining blood pressure of the user 102.

In some examples, external pressure may be applied to the optical sensor when the user 102 grabs an object, when the user 102 has swollen extremities (e.g., fingers) due to dehydration, or the like. In some instances, the PPG system 235 may be unable to transmit light through different skin tissue layers when the pressure between the optical sensor and the skin of the user 102 is increased. That is, the system 200 may instruct the user 102 to apply different pressures to observe how different wavelengths/PPG waveforms respond to changing pressures. As such, the system 200 may determine how PPG data (e.g., PPG waveforms of different wavelengths) change in response to varying pressures applied between the wearable device 104 and the tissue of the user. In this regard, the system 200 may use morphological features associated with respective PPG waveforms when pressure is applied to account for changes in blood pressure metrics of the user 102. Moreover, in some aspects, pressure sensors (e.g., piezoelectric sensors) may be used identify vibrations or other pressure changes attributable to heartbeats, which may be used to determine when heartbeats are detected (e.g., pulse arrival times), and may therefore be used to determine blood pressure metrics for the user.

In some aspects, the system may be configured to identify other circumstances or characteristics of the wearable device 104 and/or the user 102 that affect signal qualities or characteristics, such as user skin temperature, ring rotation/fit (e.g., tightness or looseness of the ring, as determined using pressure sensors or PPG sensors). In such cases, the system may be configured to identify how such characteristics affect morphological features, and compensate for such characteristics when determining morphological features of PPG waveforms. That is, PPG signals may be compensated using data from other sources, such as pressure sensors, temperature sensors, and the like.

In some aspects, the system 200 may determine the first set of morphological features associated with the first PPG waveform based on a first systolic peak and a first diastolic peak corresponding to the heartbeat (e.g., heartbeat pulse) for the first PPG waveform. Further, the system 200 may determine the second set of morphological features associated with the second PPG waveform based on a second systolic peak and a second diastolic peak corresponding to the heartbeat for the second PPG waveform. That is, the system 200 may compare the first set of morphological features and the second set of morphological features to determine one or more blood pressure metrics of the user 102.

For example, the system 200 may determine correlation coefficients between each of the PPG waveforms of different wavelengths, delays between systolic and diastolic peaks of a second derivative of the PPG waveforms of different wavelengths, and differences in systolic peak timings between PPG waveforms of different wavelengths. That is, blood pressure of the user 102 may be determined (e.g., estimated) using the morphological features displayed by multiple PPG pulses. As such, the system 200 may use the wearable device 104 placed at relative locations on the user 102 to acquire PPG data using via the PPG system 335, to determine morphological features from the PPG waveforms, and to determine one or more blood pressure metrics of the user 102 based on a comparison of morphological features. Further, the system 200 may determine blood pressure metrics of the user 102 and may utilize acceleration data from the one or more motion sensors 245 to selectively adjust the blood pressure metrics of the user 102.

Analysis of various morphological features of PPG waveforms that may be used to determine blood pressure metrics will be further shown and described with reference to FIG. 4.

In some aspects, the system 200 may transfer physiological data, such as PPG data, acceleration data, pressure data, and the like, acquired from various physiological locations and/or penetration depths from the one or more wearable devices 104 to the one or more user devices 106. Subsequently, the user device 106 (and/or other components of the system 200, such as servers 110) may determine blood pressure metrics of the user 102 based on the received physiological data. In some aspects, the user device 106 may store blood pressure trends for the user 102 in the database 265. That is, the blood pressure trends may indicate normal (e.g., typical) blood pressure levels of the user 102 and may indicate a baseline blood pressure metric associated with the user 102. Further, the user device 106 may compare the current blood pressure metric to the baseline blood pressure metric for differences (e.g., deviations). In some cases, the user 106 may determine notable differences between the baseline blood pressure metric of the user 102 and the current blood pressure metric of the user 102 and may use a GUI 275 of the user device 106 to display information associated with the differences. As such, the GUI 275 may alert (e.g., notify) the user about current blood pressure metrics of the user 102 in comparison to typical blood pressure trends of the user 102 and/or additional instructions for the user 102 to follow in order to calibrate blood pressure metrics.

Figure 3:
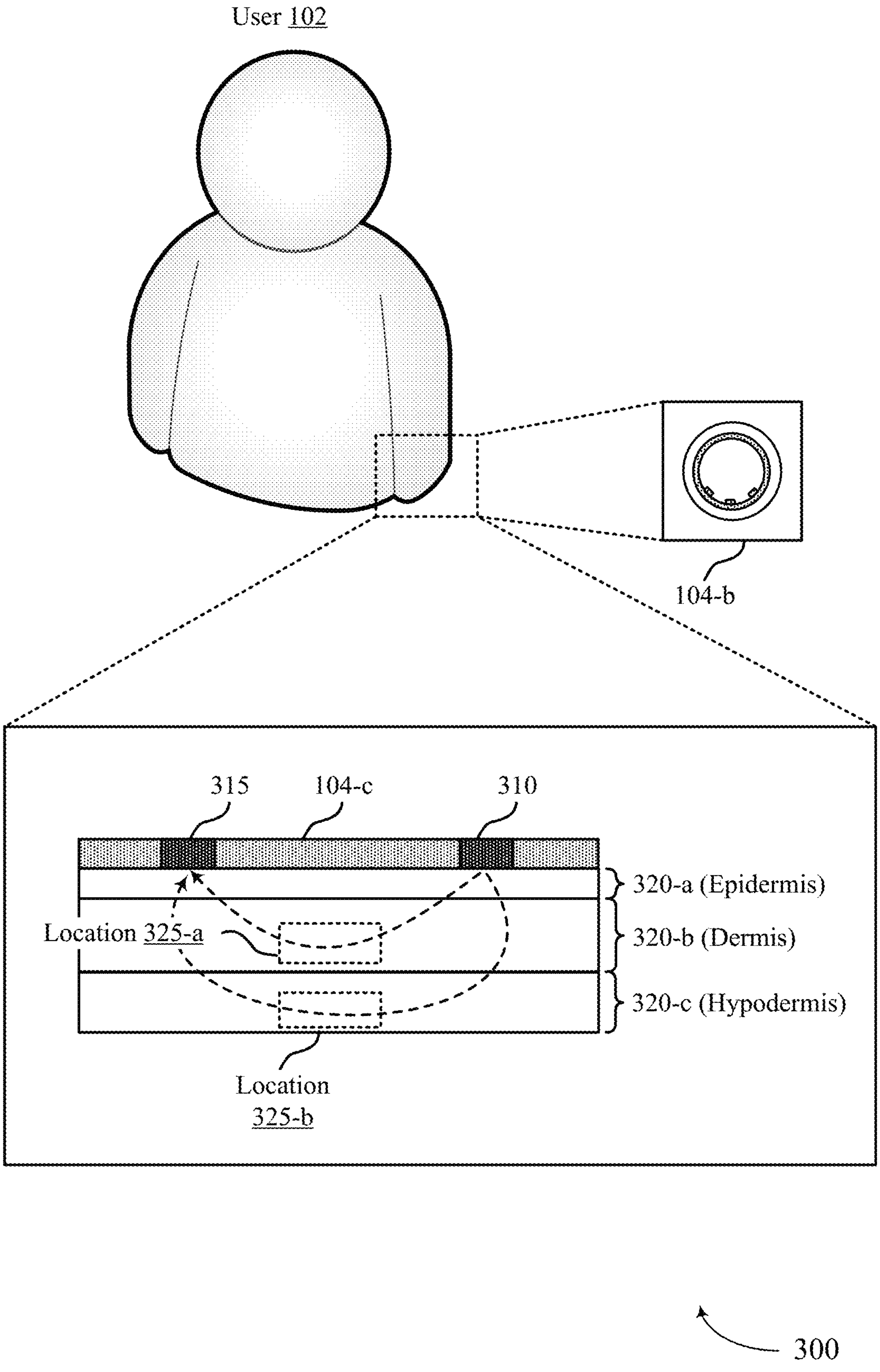
FIG. 3 illustrates an example of a wearable device system that supports techniques for determining blood pressure based on morphological features of pulses in accordance with aspects of the present disclosure.

FIG. 3 illustrates an example of a wearable device system 300 that supports techniques for determining blood pressure based on morphological features of pulses in accordance with aspects of the present disclosure. In some implementations, the wearable device system 300 may implement, or be implemented by, aspects of the system 100 and the system 200, as described with reference to FIGS. 1 and 2.

For example, the wearable device system 300 may be implemented by a wearable device 104 (e.g., a ring 104), a user device 106, one or more servers 110, or any combination thereof. In the following description of the wearable device system 300, the operations may be performed in a different order than the example order shown, or the operations may be performed in different orders or at different times. Some operations may also be omitted from the wearable device system 300, and other operations may be added to the wearable device system 300. In this example, the wearable device system 300 may be referred to as a system 300. Accordingly, the term "a wearable device 104-*b*" may be used interchangeably with "a wearable ring device," unless noted otherwise herein.

In the example of FIG. 3, the system 300 may use one or more wearable devices 104 (e.g., wearable device 104-*b*) to determine a blood pressure metric for the user 102 based on morphological features of PPG data acquired using the respective wearable devices. For example, the wearable device 104-*b* may use PPG techniques that include a triple LED (e.g., red, green, and IR) system that enables the wearable device 104-*b* to propagate multiple light waves into different tissue layers 320 of the user 102 based on the wavelength of light. That is, the penetration depth (e.g., wavelength range) of light into the skin of the user 102 increases with wavelength from the UV to the visible light range and through the IR range.

In the system 300, a light emitting component 310 (e.g., LED) and a photodetector 315 may be coupled to a controller to transmit light to locations 325 associated with one or more wavelengths and acquire measurements. In this example, the light emitting component 310 may transmit first light associated with a wavelength range (e.g., IR light, red light, etc.) that penetrates to a depth or location 325-*a* at the epidermis layer 320-*a*, where the first light travels back to the photodetector 315 with acquired PPG data. Additionally, the light emitting component 310 may transmit second light associated with a wavelength range (e.g., red light, green light, blue light, etc.) that penetrates to a depth or location 325-*b* at the hypodermis layer 320-*c*, where the second light travels back to the photodetector 315 with additional acquired PPG data.

In other words, the wearable device 104-*b* may utilize light of different wavelength ranges to acquire PPG data at different locations 325 or penetration depths of the tissue of the user. That is, the system 300 may enable the controller of the wearable device 104-*b* to transmit a blue light associated with a wavelength of approximately 460 nanometers (nm), a green light associated with a wavelength of approximately 530 nm, a red light associated with a wavelength of approximately 660 nm, or an IR light associated with a wavelength of approximately 940 nm, where each of the transmitted waves of light may reach one or more tissue layers 320 (e.g., an epidermis layer 320-*a* at around 0.3 millimeters (mm), a dermis layer 320-*b* at around 1.0 mm, a hypodermis layer 320-*c* at around 3.0 mm). That is, each of the transmitted lights may reach the one or more layers of tissues where the blood vessels are located, such as the capillaries located closest to the skin of the user 102 at the epidermis, the arterioles located at the middle layer at the dermis, and the arteries located at the deepest layer at the hypodermis. As such, the system 300 may use a light emitting component 310 and photodetector 315 coupled to a controller on the wearable device 104-*b* to transmit one or more lights associated with wavelength ranges to one or more tissue layers 320 at multiple locations 325 to acquire PPG data.

Further, the single wearable device 104-*b* may transmit the first and second light from the light emitting component 310 through one or more tissue layers 320 and back to the photodetector 315 to acquire PPG data during a time interval, where the time interval may include a heartbeat of the user 102. In some examples, the wearable device 104-*b* may acquire PPG data based on the first light and the second light via the photodetector 315. The PPG data may include a first PPG waveform acquired via the first light associated with the first wavelength and a second PPG waveform acquired using the second light associated with the second wavelength.

Moreover, each of the PPG waveforms, such as the first PPG waveform and the second PPG waveform, may depict different morphological features. That is, the wearable device 104-*b* may determine a first set of morphological features associated with the first PPG waveform based on a first systolic peak and a first diastolic peak corresponding to the heartbeat within the first PPG waveform. Further, the wearable device 104-*b* may determine a second set of morphological features associated with the second PPG waveform based on a second systolic peak and a second diastolic peak corresponding to the heartbeat within the second PPG waveform. As such, the wearable device 104-*c* may acquire PPG data from one or more wavelengths traveling to different tissue penetration depths (e.g., the epidermis layer 320-*a*, the dermis layer 320-*b*, at the hypodermis layer 320-*c*). Thus, the system 300 may use a single wearable device 104-*b* to transmit respective lights associated with respective wavelengths, acquire PPG data from the user 102, determine respective sets of morphological features associated with each of the PPG waveforms, and determine one or more blood pressure metrics for the user 102 based on the comparison of respective sets of morphological features.

In some cases, light emitted by light emitting components 310 of the wearable device 104-*b* (e.g., LEDs) may be measured by multiple photodetectors 315. In some cases, the light emitting components 310 and photodetectors 315 may be positioned at different radial positions on an inner circumferential surface of the wearable device 104-*b*. For example, in some cases, multiple light emitting components 310 and multiple PDs may be arranged around the inner circumferential surface of the wearable device 104-*b* in in an interleaving pattern (e.g., LED, PD, LED, PD) at regular or irregular spacings between the respective components. In other cases, multiple photodetectors 315 may be positioned adjacent to one another at a same or similar radial position of the wearable device 104-*b*.

In some cases, measuring light with multiple photodetectors 315 (e.g., multiple photodetectors 315 that are the same distance away from a common light-emitting component 310) may enable the wearable device 104-*b* to determine phase differences in light signals received at the respective photodetectors 315. Such parallel measurement of light by multiple photodetectors 315 may enable more robust and reliable PPG data collection. For example, in some cases, phase differences between light measured at multiple PDs 315 may be used to determine a velocity of blood moving throughout the blood vessels, which may be used to further determine or estimate blood pressure.

Various morphological features of PPG waveforms which may be used to determine blood pressure metrics may be further shown and described with reference to FIG. 4.

Figure 4:
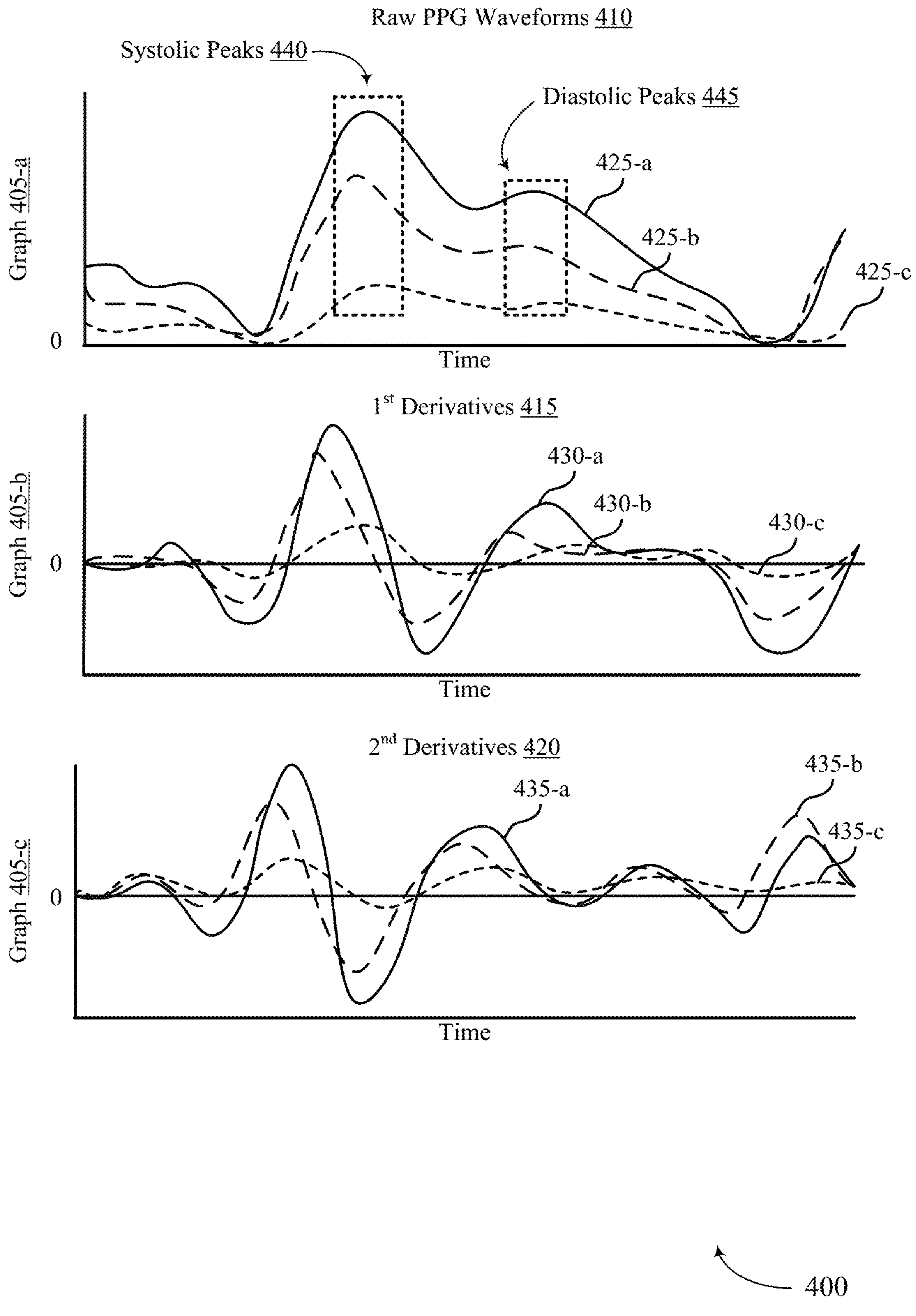
FIG. 4 illustrates an example of pulse morphology graphs that supports techniques for determining blood pressure based on morphological features of pulses in accordance with aspects of the present disclosure.

FIG. 4 illustrates an example of pulse morphology graphs 400 that supports techniques for determining blood pressure based on morphological features of pulses in accordance with aspects of the present disclosure. In some implementations, the pulse morphology graphs 400 may implement, or be implemented by, aspects of the system 100, the system 200, and the system 300, as described with reference to FIGS. 1-3. For example, the pulse morphology graphs 400 may illustrate PPG data acquired from a user via a wearable device 104 (e.g., a ring 104), a user device 106, one or more servers 110, or any combination thereof. In the following description of the pulse morphology graphs 400, the operations may be performed in a different order than the example order shown, or the operations may be performed in different orders or at different times. Some operations may also be omitted from the pulse morphology graphs 400, and other operations may be added to the pulse morphology graphs 400.

In the example of FIG. 4, the pulse morphology graphs 400 may display multiple graphs 405. That is, each of the graphs 405 may illustrate varying signal strengths over time and may display different morphological features (e.g., size of pulses, shape of pulses). In graph 405-*a*, raw PPG waveforms 410 (e.g., raw PPG signals) may be depicted. For example, the raw PPG waveforms 410 may represent a raw IR PPG signal 425-*a*, a raw red PPG signal 425-*b*, and a raw green PPG signal 425-*c*. That is, each of the raw PPG waveforms 410 may vary in signal strength over time and may display different morphological features (e.g., peaks, troughs). Further, each of the raw PPG waveforms 410 may include one or more systolic peaks and one or more diastolic peaks. In some examples, a wearable device may transmit one or more lights associated with wavelengths during a time interval with the heartbeat of a user. That is, the wearable device may receive the transmitted light and acquire PPG data from the user in the form of raw PPG waveforms 410.

In some examples, the raw PPG waveforms 410 may exhibit PPG data acquired at different penetration depths due to different wavelengths of light used, as described herein. Further, each of the raw PPG waveforms 410 may represent measurements of one or more lights associated with wavelength ranges to one or more tissue layers at multiple locations. As such, the graph 405-*a* may depict signal strengths where the raw IR PPG signal 425-*a* exceeds the raw red PPG signal 425-*b* and the raw green PPG signal 425-*c* during the time interval.

In some implementations, first derivatives 415 may be calculated for each of the raw PPG waveforms 410. That is, graph 405-*b* may depict slope signals 430-*a*, 430-*b*, and 430-*c* of the raw PPG signals 425-*a*, 425-*b*, and 425-*c*, respectively. In this regard, because the first derivatives 415 are derived from the raw PPG waveforms 410, characteristics/features of the first derivatives 415 may be considered to be morphological features of the respective raw PPG waveforms 410.

Each of the raw PPG waveforms 410 may be filtered (e.g., a bandpass filtered PPG signal) and respective first derivatives 415 (e.g., slope signals 430) may be calculated for each of the raw PPG waveforms 410 for display in graph 405-*b*. In some examples, the first derivative may be identified as a velocity PPG (VPG), where one or more salient positive peaks found in the first derivatives 415 indicate points in time where the raw PPG waveforms 410 is growing at a highest rate. Hence, the VPG shows the velocity of the raw PPG waveforms 410 and may represent the systolic rise and the diastolic rise of the PPG pulse waveforms.

In some aspects, second derivatives 420 may be calculated for each of the raw PPG waveforms 410 (e.g., raw PPG signals 425). That is, graph 405-*c* may depict second derivatives (e.g., curvature signals 435-*a*, 435-*b*, and 435-*c*) of the raw PPG signals 435-*a*, 435-*b*, and 435-*c*, respectively. In this regard, because the second derivatives 420 are derived from the raw PPG waveforms 410, characteristics/features of the second derivatives 420 may be considered to be morphological features of the respective raw PPG waveforms 410.

Each of the raw PPG waveforms 410 may be additionally filtered and respective second derivatives 420 may be calculated for each of the raw PPG waveforms 410 for display in graph 405-*c*. In some cases, the second derivatives 420 (e.g., curvature signals 435) may be identified as an acceleration PPG (APG), where multiple peaks are identified for blood pressure assessment. In FIG. 4, the second derivatives 420 may illustrate five peaks that include some upward peaks and downward peaks present for measured PPG pulses. That is, one or more timings of APG peaks (e.g., a number of samples after a pulse starts), one or more ratios, and one or more computed features may be used as inputs for a classifier that maps the feature values into blood pressure metrics. As such, identifying peaks for second derivatives 420 may enable the system to determine accurate blood pressure metrics for the user.

In some aspects, one or more morphological features of the raw PPG waveforms 410 may be identified from the graphs 405-*a*, 405-*b*, and 405-*c*. That is, the graph 405-*a* may illustrate the raw PPG waveforms 410 that may be identified as one or more PPG waveforms. In some implementations, a system may determine a correlation coefficient between the raw IR PPG signal 425-*a* and the raw red PPG signal 425-*b*. However, in other examples, the system may determine correlation coefficients between various PPG signals with various wavelength ranges and are not limited to only the raw IR PPG signal 425-*a* for a first wavelength range and the raw red PPG signal 435-*b* for a second wavelength range. That is, the system may compare morphological features of the raw PPG waveforms 410 that are displayed on the graph 405-*a*, such as one or more systolic peaks 440 and diastolic peaks 445 to determine blood pressure metrics. As such, the raw PPG waveforms 410 that represent multiple PPG waveforms may include respective sets of morphological features that the system may utilize to determine accurate blood pressure metrics of the user.

In some examples, the graph 405-*a* may illustrate the raw PPG waveforms 410 that indicate systolic peak 440 timings for systolic blood pressure. That is, the graph 405-*a* may illustrate one or more delays of the systolic peaks 440 of the raw PPG waveforms 410. Specifically, the graph 405-*a* may depict one or more delays between a first wavelength that includes a first wavelength range associated with the raw IR PPG signal 425-*a* and a second wavelength that includes a second wavelength range associated with the raw green PPG signal 425-*c*. Further, the system may determine timings based on the systolic peaks 440 of the raw PPG waveforms 410. For example, the system may determine a first timing of the systolic peak 440 of the raw IR PPG signal 425-*a* (e.g., the first PPG waveform), and a second timing of the systolic peak 440 of the raw green PPG signal 425-*c* (e.g., the second PPG waveform), where the first set of morphological features and the second set of morphological features includes the first timing and the second timing. The system may determine a delay between the systolic peak 440 of the raw IR PPG signal 425-*a* and the systolic peak 440 of the raw green PPG signal 425-*c* based on the first timing and the second timing. As such, the system may use the delay to determine blood pressure metrics of the user.

Additionally, or alternatively, additional morphological features may be identified from the graph 405-*a*. That is, the graph 405-*a* may depict the raw PPG waveforms 410 calculated from predicting blood pressure metrics from single pulses. That is, the raw PPG waveforms 410 may represent systolic, diastolic, and mean average blood pressures. Accordingly, the system may identify a morphological feature, such as a ratio of area under each of the PPG waveforms 410 (e.g., features=area under the curve for the raw IR PPG signal 425-*a* (AUC_IR)/area under the curve for the raw green PPG signal 425-*c* (AUC_GRE)) that compares areas under one or more curves from different phases of PPG pulses. As such, the system may use this morphological feature of calculating the area under one or more curves of the graph 405-*a* to determine blood pressure metrics of the user.

In some aspects, additional morphological features may be identified from the graph 405-*b*. That is, the graph 405-*b* may depict the first derivatives 415 (e.g., slope signals 430) calculated for each of the raw PPG waveforms 410 illustrated in graph 405-*a*. That is, the first derivatives 415 may be calculated from predicting blood pressure metrics from single pulses. That is, the first derivatives 415 may represent systolic blood pressures. Accordingly, the system may identify a morphological feature, such as a ratio of maximal slopes between the first derivatives 415 of the PPG waveforms 410. In other words, a morphological feature that may be used to determine blood pressure may include a ratio of the maximum slopes of the raw PPG signals 425 (and/or ratio of the peaks of the slope signals 430) (e.g., feature=maximum slope for the red PPG signal 425-*b* depicted as peak of the red slope signal 430-*b* (MS_RED)/maximum slope for the raw green PPG signal 425-*c* depicted as the peak of the green slope signal 430-*c* (MS_GRE)). As such, the system may use morphological features including the maximum slopes of the raw PPG signals 425 in graph 405-*a* (e.g., peaks of the slope signals 430 in the graph 405-*b*) to determine blood pressure metrics of the user.

In some implementations, one or more morphological features may be identified from the graph 405-*c*. That is, the graph 405-*c* may illustrate the second derivatives 420 (e.g., curvature signals 435) of the raw PPG waveforms 410 illustrated in graph 405-*a*, such as second derivatives of the raw PPG waveforms 410. In other examples, the graph 405-*c* may depict the second derivatives 420 that represent diastolic pressure and mean average blood pressures. In some aspects, a system with a controller that couples one or more light emitting components to one or more photodetectors may determine a curvature signals 435-*a*, 435-*b*, and 435-*c* of the raw PPG signals 425-*a*, 425-*b*, and 425-*c*, respectively (e.g., the second derivatives of the raw PPG waveforms 410).

That is, the system may determine peaks of the curvature signals 435 corresponding to the systolic peaks 440 the raw PPG signals 425, where morphological features of the respective PPG waveforms 410 include the timings of the peaks of the respective curvature signals 435. In particular, the system may determine relative delays between the timings of the peaks of the curvature signals 435, and may use the relative timings of the peaks (e.g., delay between peaks of the curvature signals 435) as a morphological feature used to determine blood pressure metrics As described previously herein, aspects of the present disclosure may utilize PPG data to determine morphological features of PPG waveforms, and may thereby use the morphological features of the PPG waveforms (e.g., morphological features shown and described in the graphs 405 of FIG. 4) to determine blood pressure metrics for a user. In some implementations, a wearable device 104 may collect PPG data in the form of one or more sets of PPG pulses (as shown in raw PPG signals 425) to measure specific physiological parameters of the user. However, not all PPG pulses may exhibit the same morphological features or characteristics. In other words, PPG pulses may exhibit varying shapes and characteristics. That is, morphological features of PPG pulses (e.g., PPG pulse amplitude, duration, slope, curvature, relationships between peaks) may vary from one PPG pulse to the next, and some of the PPG pulses may inaccurately represent a physiological measurement. Additionally, or alternatively, factors such as light, pressure, a posture of the user (e.g., the user is sitting or standing), or a hydration of the user (e.g., the user may have swollen fingers due to lack of hydration) may affect the accuracy of the PPG data. In particular, a system that uses the inaccurate PPG pulses or fails to account for additional factors that affect the PPG data may result in unreliable physiological measurements. That is, multiple systems may benefit from one or more techniques for identifying PPG pulses that accurately represent the physiological metrics of one or more users.

Accordingly, in some implementations, the systems of the present disclosure may be configured to identify one or more "representative" (e.g., common, average) PPG pulses that accurately represents the physiological metrics of the user, and may utilize identified, representative PPG pulses of PPG waveforms to identify morphological features and/or blood pressure measurements. That is, techniques described herein may be used to identify the PPG pulses that are of high quality and accurately reflect physiological metrics of the user in order to determine blood pressure measurements.

To identify the one or more PPG pulses that accurately represents the physiological metrics of the user (e.g., identify PPG pulses that will be used to determine pulse observation times and/or blood pressure metrics), a wearable device 104 may acquire PPG data that includes a first set of PPG pulses from the user. In some aspects, the system may compare multiple morphological features from the first set of PPG pulses for each specific physiological measurement. Further, the system may determine one or more PPG profiles (e.g., one or more representative PPG pulses, one or more common pulse templates) for each specific physiological metric based on the comparison of the multiple morphological features of the first set of PPG pulses. That is, each of the one or more PPG profiles may include a set of multiple morphological value ranges for the multiple morphological features. In some examples, each of the PPG profiles may represent a representative (e.g., common, average) pulse calculated from the first set of PPG pulses for each specific physiological measurement.

In addition, the system may acquire additional PPG data from the user via the wearable device 104. In some cases, the system may acquire the additional PPG data from the user as a second set of PPG pulses. In some implementations, the system may determine that one or more PPG pulses from the second set of PPG pulses match the one or more PPG profiles from the first set of PPG pulses. That is, the system may detect that multiple morphological feature values of the second set of PPG pulses satisfy the multiple morphological value ranges of the one or more PPG profiles. In other words, the system may identify which PPG pulses of the second set of PPG pulses "match" the PPG profiles.

Subsequently, the system may determine one or more physiological metrics associated with the user based on the one or more PPG pulses from the second set of PPG pulses matching the one or more PPG profiles from the first set of PPG pulses. Stated differently, the system may utilize the PPG pulses that "match" the PPG profiles (e.g., the system may utilize "representative" PPG pulses) to perform physiological measurements for the user. For example, the system/wearable device 104 may be configured to utilize PPG pulses within PPG waveforms that match the PPG profiles to determine morphological features, and therefore determine blood pressure measurements.

Conversely, the system may detect that the one or more PPG pulses from the second set of PPG pulses fails to match the one or more PPG profiles from the second set of PPG pulses and may refrain from using that specific physiological metric associated with the user or otherwise take this information into account. In other words, the system/wearable device may not utilize PPG pulses within PPG waveforms that do not match PPG profiles to determine morphological features and/or blood pressure measurements.

In some aspects, the wearable device may identify the one or more representative PPG pulses for each user using the existing hardware features of the wearable device. In some examples, the system may define the one or more PPG pulse profiles (e.g., one or more PPG templates) that represent common PPG pulses of the user. That is, the system may acquire one or more PPG pulses and may compare each of the PPG pulses to each other to determine the one or more PPG pulse profiles. In such cases, the system may determine the one or more PPG profiles by identifying common (e.g., average) values (e.g., average length, amplitude, slope, or the like) of the multiple PPG pulses. For example, the system may define one or more PPG pulse profiles based on common PPG pulses acquired from the user via a day-time calibration sequence. That is, the calibration sequence may be initiated to define valid samples to determine which of the PPG pulses are suitable (e.g., reliable) for performing physiological measurements. In some cases, the system may utilize a changing correlation between different signal paths to find an optimal measurement time for the PPG pulses.

In some implementations, the system may account for posture estimation of the user, and may determine different sets of PPG profiles based on different postures of the user. For example, the system may detect the posture of the user (e.g., the user may be standing, sitting, lying down, or the like) which may affect the signal quality metrics of the PPG pulses. As such, the system may use the PPG pulse profiles, the calibration sequence, and additional factors to select accurate PPG pulses with appropriate signal quality metrics that represent the physiological metrics of the user (e.g., first set of PPG profiles for when the user is standing, and second set of PPG profiles for when the user is sitting).

Figure 5:
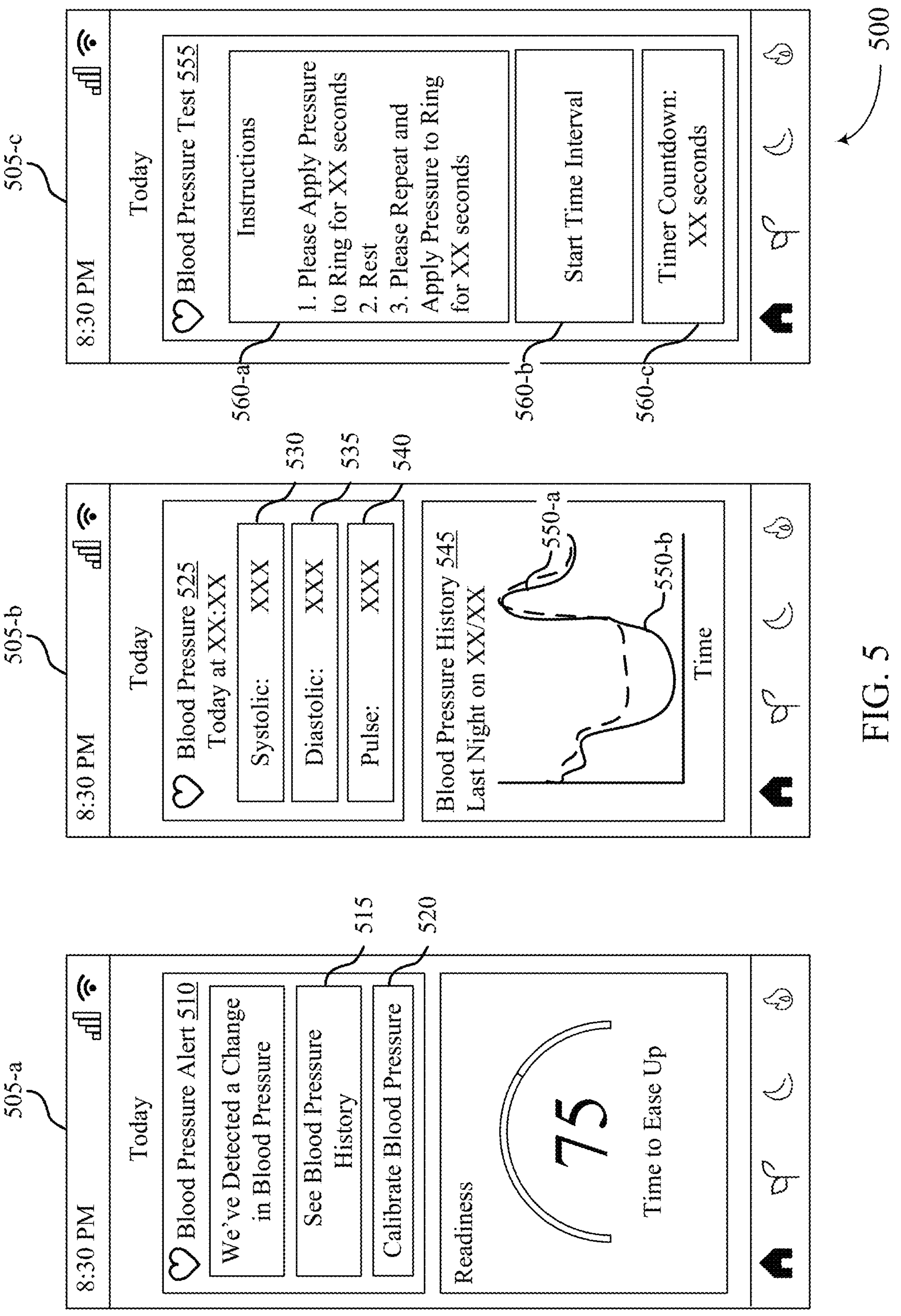
FIG. 5 illustrates an example of a graphical user interface (GUI) that supports techniques for determining blood pressure based on morphological features of pulses in accordance with aspects of the present disclosure.

FIG. 5 illustrates an example of a GUI 500 that supports techniques for determining blood pressure based on morphological features of pulses in accordance with aspects of the present disclosure. The GUI 500 may implement, or be implemented by, aspects of the system 100, the system 200, the system 300, and the pulse morphology graph 400, or any combination thereof. For example, the GUI 500 may be implemented for a user at a user device connected to a wearable device (e.g., a wearable ring device, watch, necklace, or any other wearable device), and that may be examples of a user 102, a user device 106, and a wearable device 104 as described with reference to FIGS. 1-4.

The GUI 500 illustrates a series of application pages, including an application page 505-*a*, an application page 505-*b*, and an application page 505-*c*, that may be displayed to a user via the GUI 500 (e.g., a user 102 and a GUI 275 as described with reference to FIGS. 1-5). In some examples, the user may open the application page 505-*a* to see scores belonging to the user. For example, the application page 505-*a* may display a Sleep Score, a Readiness Score, and the like. In some examples, the application page 505-*a* may illustrate a blood pressure alert 510 that shows alerts for the user. For example, the blood pressure alert 510 may indicate that a change of blood pressure of the user was detected. That is, the user may select a blood pressure history 515 of the user. Additionally, or alternatively, the user may decide that blood pressure measurements for the user may need to be calibrated again. That is, the user may have experienced a change that has affected blood pressure metrics. For example, the user may have traveled to a higher elevation and is experiencing swollen extremities (e.g., fingers) due to dehydration. Further, the user may select a box to calibrate blood pressure 520 to enable the wearable device to acquire accurate blood pressure metrics.

In some examples, the user may select the blood pressure history 515 feature and the application page 505-*b* may appear on the user device. The application page 505-*b* may show a blood pressure 525 acquired at the current day and a specific (e.g., current) time. In some examples, the blood pressure 525 may depict several measurements, such as a systolic blood pressure 530 measured from one or more arteries when the heart of the user beats and a diastolic blood pressure 535 measured from one or more arteries when the user's heart is in between heart beats. In some examples, a classification of blood pressure may include either a normal blood pressure or a high blood pressure. For the user, a normal blood pressure may indicate a systolic blood pressure of less than 130 mmHg and a diastolic blood pressure of less than 80 mmHg. Alternatively, a high blood pressure may indicate a systolic blood pressure greater than 130 mmHg and a diastolic blood pressure greater than 80 mmHg. Additionally, a pulse 540 may be displayed and represents a measurement of heart rate (e.g., number of times the user's heart beats per minute). Further, the pulse 540 may be calculated by subtracting the diastolic blood pressure 535 from the systolic blood pressure 525.

Additionally, or alternatively, the application page 505-*b* may illustrate a blood pressure history 545 of the user for a specific term. In the example of FIG. 5, the blood pressure history 545 depicts a night term for a specific date with two trendlines. That is, the blood pressure history 545 may illustrate a baseline (e.g., normal, typical, trend) blood pressure metric 550-*a* associated with the user and a blood pressure metric 550-*b* for the night term at the specific date. That is, application page 505-*b* of the user device may graphically illustrate comparisons between the blood pressure metric 550-*a* that represents typical blood pressure trends for a typical night term of the user to the blood pressure metric 550-*b* that represents the blood pressure trends for the last night term of the user. That is, the GUI 500 may display and/or indicate information associated with the difference between the baseline blood pressure metric 550-*a* and the blood pressure metric 550-*b* (e.g., your blood pressure is ±X compared to your average blood pressure).

In some examples, the GUI 500 may share information that may be indicative of whether the user has nocturnal hypertension based on a dipping of pulses. For the user, a normal, nocturnal blood pressure trend may indicate a blood pressure dipping about 10% to 15% less than typical daytime pulses. However, detecting blood pressure changes (e.g., blood pressure changes based on absolute values and additional values) greater than 15% may indicate a warning that the user has an elevated sodium level, a salt sensitivity, CKD, CHF, diabetes, a structural vascular disease, insomnia, or the like. That is, the user may look at the blood pressure history 545 over time periods to determine whether blood pressure metrics 550 may point to possible cardiovascular health risks.

In some examples, the user may select the blood pressure calibration 520 feature and the application page 505-*c* may appear on the user device. In such examples, the user may select the blood pressure calibration 520 feature and may undergo a blood pressure test 555. That is, the application page 505-*c* may indicate that the user may take the blood pressure test 555 and to follow a set of instructions. For example, an instruction box 560-*a* may indicate for the user to apply a first pressure to the wearable device (e.g., press against the wearable device, clench fists to apply pressure to a wearable ring) for some specified time during a time interval, to rest (e.g., pause) and not apply respective pressure to the ring to lower the pressure to a normative state, and to again apply a second pressure to the wearable device for another specified time during the time interval. Further, the blood pressure test 555 may display one or more interval boxes, in FIG. 5, a time interval 560-*b* box enables the user to start the time interval period for applying respective pressures to the wearable device. That is, a timer countdown 560-*c* box may indicate time in seconds for the user to apply the first pressure and when to apply the second pressure, or a time period in seconds for the user to rest in between time intervals. In some cases, the user may refrain from applying additional pressure to the wearable device but may select the blood pressure calibration 520 feature for the user device to collect one or more blood pressure trends of the user. As such, the blood pressure test 555 may calibrate blood pressures of the user and may create one or more blood pressure trends that accurately represent the blood pressures of the user. Further, the user device may display the blood pressure test 555 that enables the wearable device to monitor pulse observation times of different pulses at variable tissue penetration depths and/or locations.

Figure 6:
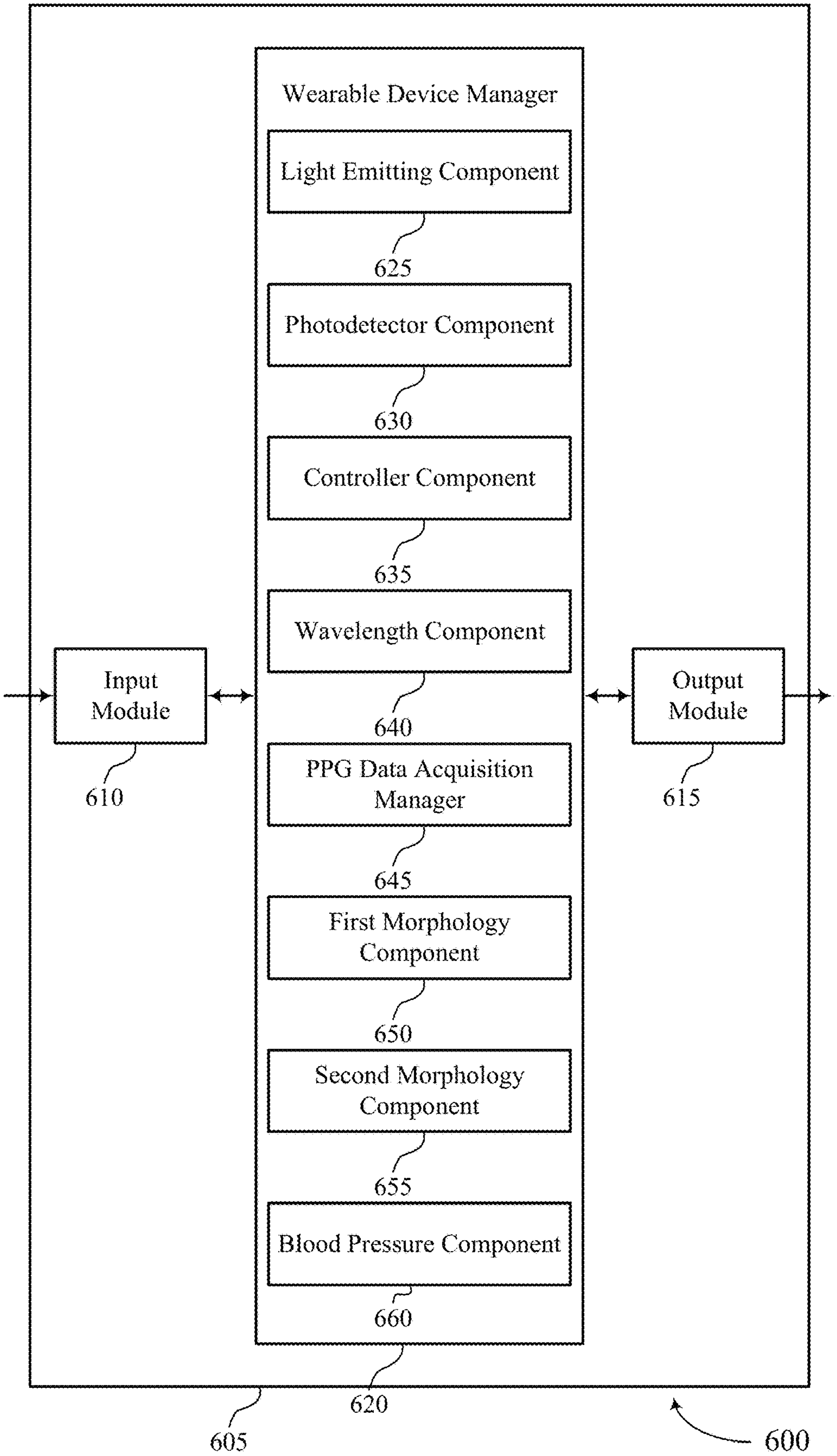
FIG. 6 illustrates a block diagram of an apparatus that supports techniques for determining blood pressure based on morphological features of pulses in accordance with aspects of the present disclosure.

FIG. 6 illustrates a block diagram 600 of a device 605 that supports techniques for determining blood pressure based on morphological features of pulses in accordance with aspects of the present disclosure. The device 605 may include an input module 610, an output module 615, and a wearable device manager 620. The device 605 may also include a processor. Each of these components may be in communication with one another (e.g., via one or more buses).

For example, the wearable device manager 620 may include a light emitting component 625, a photodetector component 630, a controller component 635, a wavelength component 640, a PPG data acquisition manager 645, a first morphology component 650, a second morphology component 655, a blood pressure component 660, or any combination thereof. In some examples, the wearable device manager 620, or various components thereof, may be configured to perform various operations (e.g., receiving, monitoring, transmitting) using or otherwise in cooperation with the input module 610, the output module 615, or both. For example, the wearable device manager 620 may receive information from the input module 610, send information to the output module 615, or be integrated in combination with the input module 610, the output module 615, or both to receive information, transmit information, or perform various other operations as described herein.

The light emitting component 625 may be configured as or otherwise support a means for one or more light-emitting components configured to emit light associated with at least a first wavelength and a second wavelength. The photodetector component 630 may be configured as or otherwise support a means for one or more photodetectors configured to receive light emitted by the one or more light-emitting components. The controller component 635 may be configured as or otherwise support a means for a controller communicatively coupled to the one or more light-emitting components and the one or more photodetectors, the controller configured to. The wavelength component 640 may be configured as or otherwise support a means for transmit, during a time interval including a heartbeat of a user and using the one or more light-emitting components, first light associated with the first wavelength and second light associated with the second wavelength. The PPG data acquisition manager 645 may be configured as or otherwise support a means for acquire PPG data from the user based at least in part on receiving the first light and the second light via the one or more photodetectors, the PPG data comprising at least a first PPG waveform acquired using the first light associated with the first wavelength and a second PPG waveform acquired using the second light associated with the second wavelength. The first morphology component 650 may be configured as or otherwise support a means for determine a first set of morphological features associated with the first PPG waveform based at least in part on a first systolic peak and a first diastolic peak corresponding to the heartbeat within the first PPG waveform. The second morphology component 655 may be configured as or otherwise support a means for determine a second set of morphological features associated with the second PPG waveform based at least in part on a second systolic peak and a second diastolic peak corresponding to the heartbeat within the second PPG waveform. The blood pressure component 660 may be configured as or otherwise support a means for determining a blood pressure metric for the user based at least in part on a comparison of the first set of morphological features and the second set of morphological features.

The PPG data acquisition manager 645 may be configured as or otherwise support a means for acquiring PPG data from a user using a wearable device, the PPG data collected during a time interval including a heartbeat of the user, the PPG data comprising at least a first PPG waveform acquired using first light associated with a first wavelength and a second PPG waveform acquired using second light associated with a second wavelength. The first morphology component 650 may be configured as or otherwise support a means for determining a first set of morphological features associated with the first PPG waveform based at least in part on a first systolic peak and a first diastolic peak corresponding to the heartbeat within the first PPG waveform. The second morphology component 655 may be configured as or otherwise support a means for determining a second set of morphological features associated with the second PPG waveform based at least in part on a second systolic peak and a second diastolic peak corresponding to the heartbeat within the second PPG waveform. The blood pressure component 660 may be configured as or otherwise support a means for determining a blood pressure metric for the user based at least in part on a comparison of the first set of morphological features and the second set of morphological features.

Figure 7:
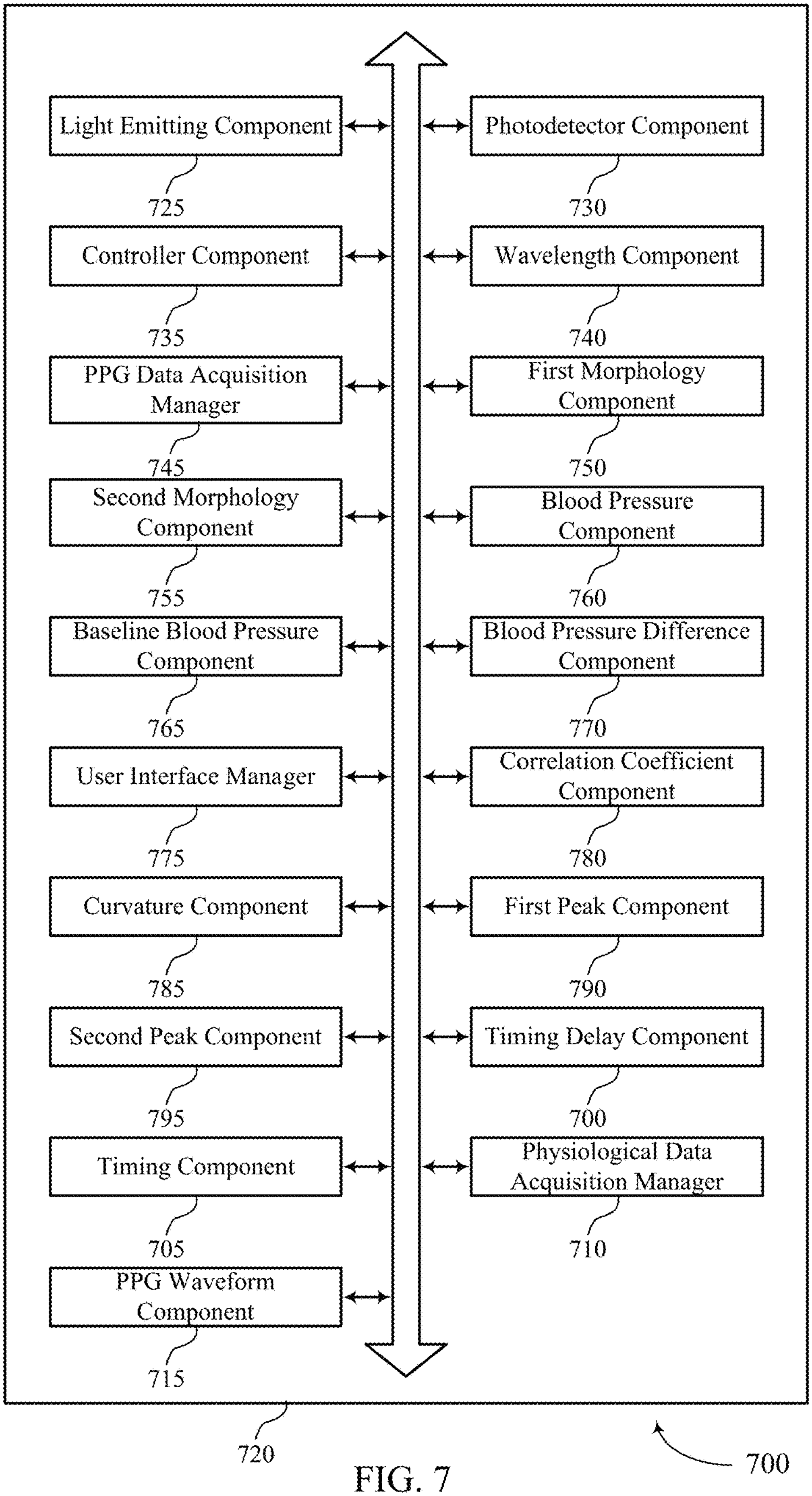
FIG. 7 illustrates a block diagram of a wearable device manager that supports techniques for determining blood pressure based on morphological features of pulses in accordance with aspects of the present disclosure.

FIG. 7 illustrates a block diagram 700 of a wearable device manager 720 that supports techniques for determining blood pressure based on morphological features of pulses in accordance with aspects of the present disclosure. The wearable device manager 720 may be an example of aspects of a wearable device manager or a wearable device manager 620, or both, as described herein. The wearable device manager 720, or various components thereof, may be an example of means for performing various aspects of techniques for determining blood pressure based on morphological features of pulses as described herein. For example, the wearable device manager 720 may include a light emitting component 725, a photodetector component 730, a controller component 735, a wavelength component 740, a PPG data acquisition manager 745, a first morphology component 750, a second morphology component 755, a blood pressure component 760, a baseline blood pressure component 765, a blood pressure difference component 770, a user interface manager 775, a correlation coefficient component 780, a curvature component 785, a first peak component 790, a second peak component 795, a timing delay component 7100, a timing component 7105, a physiological data acquisition manager 7110, a PPG waveform component 7115, or any combination thereof. Each of these components may communicate, directly or indirectly, with one another (e.g., via one or more buses).

The light emitting component 725 may be configured as or otherwise support a means for one or more light-emitting components configured to emit light associated with at least a first wavelength and a second wavelength. The photodetector component 730 may be configured as or otherwise support a means for one or more photodetectors configured to receive light emitted by the one or more light-emitting components. The controller component 735 may be configured as or otherwise support a means for a controller communicatively coupled to the one or more light-emitting components and the one or more photodetectors, the controller configured to. The wavelength component 740 may be configured as or otherwise support a means for transmit, during a time interval including a heartbeat of a user and using the one or more light-emitting components, first light associated with the first wavelength and second light associated with the second wavelength. The PPG data acquisition manager 745 may be configured as or otherwise support a means for acquire PPG data from the user based at least in part on receiving the first light and the second light via the one or more photodetectors, the PPG data comprising at least a first PPG waveform acquired using the first light associated with the first wavelength and a second PPG waveform acquired using the second light associated with the second wavelength. The first morphology component 750 may be configured as or otherwise support a means for determine a first set of morphological features associated with the first PPG waveform based at least in part on a first systolic peak and a first diastolic peak corresponding to the heartbeat within the first PPG waveform. The second morphology component 755 may be configured as or otherwise support a means for determine a second set of morphological features associated with the second PPG waveform based at least in part on a second systolic peak and a second diastolic peak corresponding to the heartbeat within the second PPG waveform. The blood pressure component 760 may be configured as or otherwise support a means for determine a blood pressure metric for the user based at least in part on a comparison of the first set of morphological features and the second set of morphological features.

In some examples, determine a baseline blood pressure metric associated with the user. In some examples, determine a difference between the baseline blood pressure metric and the blood pressure metric. In some examples, cause a GUI of a user device to display information associated with the difference between the baseline blood pressure metric and the blood pressure metric.

In some examples, determine a correlation coefficient between the first PPG waveform and the second PPG waveform based at least in part on the comparison of the first set of morphological features and the second set of morphological features, wherein the blood pressure metric is based at least in part on the correlation coefficient.

In some examples, the first wavelength comprises a first wavelength range associated with IR light. In some examples, the second wavelength comprises a second wavelength range associated with red light.

In some examples, determine a first curvature signal associated with a relative curvature of the first PPG waveform, and a second curvature signal associated with a relative curvature of the second PPG waveform. In some examples, determine a first peak of the first curvature signal corresponding to the first systolic peak of the first PPG waveform, wherein the first set of morphological features comprises a first timing of the first peak. In some examples, determine a second peak of the second curvature signal corresponding to the second systolic peak of the second PPG waveform, wherein the second set of morphological features comprises a second timing of the second peak. In some examples, determine a delay between the first timing of the first peak and the second timing of the second peak based at least in part on the comparison of the first and second sets of morphological features, wherein the blood pressure metric is based at least in part on the delay.

In some examples, the first curvature signal and the second curvature signal comprise second derivatives of the first PPG waveform and the second PPG waveform, respectively.

In some examples, the first wavelength comprises a first wavelength range associated with IR light, red light, or both. In some examples, the second wavelength comprises a second wavelength range associated with green light.

In some examples, determine a first timing of the first systolic peak of the first PPG waveform, and a second timing of the second systolic peak of the second PPG waveform, wherein the first set of morphological features and the second set of morphological features comprise the first timing and the second timing, respectively. In some examples, determine a delay between the first systolic peak of the first PPG waveform and the second systolic peak of the second PPG waveform based at least in part on the first timing and the second timing, wherein the blood pressure metric is based at least in part on the delay.

In some examples, the first wavelength comprises a first wavelength range associated with red light. In some examples, the second wavelength comprises a second wavelength range associated with green light.

In some examples, the PPG data is acquired during a time interval that a pressure between the wearable device and a tissue of the user is changed from a first pressure to a second pressure. In some examples, the first set of morphological features and the second set of morphological features comprise responses of the first PPG waveform and the second PPG waveform, respectively, to the change from the first pressure to the second pressure.

In some examples, cause a GUI of a user device to display instructions for the user to selectively change the pressure from the first pressure to the second pressure during the time interval, wherein acquiring the PPG data throughout the time interval is based at least in part on the instructions.

In some examples, acquire physiological data from the user via the wearable device, the physiological data comprising at least the PPG data and acceleration data associated with movement of the user. In some examples, selectively adjust the blood pressure metric based at least in part on the acceleration data.

In some examples, the wearable device comprises a wearable ring device.

In some examples, the first set of morphological features comprises a first amplitude of the first systolic peak, the first diastolic peak, or both. In some examples, the second set of morphological features comprises a second amplitude of the second systolic peak, the first diastolic peak, or both.

In some examples, the PPG data acquisition manager 745 may be configured as or otherwise support a means for acquiring PPG data from a user using a wearable device, the PPG data collected during a time interval including a heartbeat of the user, the PPG data comprising at least a first PPG waveform acquired using first light associated with a first wavelength and a second PPG waveform acquired using second light associated with a second wavelength. In some examples, the first morphology component 750 may be configured as or otherwise support a means for determining a first set of morphological features associated with the first PPG waveform based at least in part on a first systolic peak and a first diastolic peak corresponding to the heartbeat within the first PPG waveform. In some examples, the second morphology component 755 may be configured as or otherwise support a means for determining a second set of morphological features associated with the second PPG waveform based at least in part on a second systolic peak and a second diastolic peak corresponding to the heartbeat within the second PPG waveform. In some examples, the blood pressure component 760 may be configured as or otherwise support a means for determining a blood pressure metric for the user based at least in part on a comparison of the first set of morphological features and the second set of morphological features.

In some examples, the baseline blood pressure component 765 may be configured as or otherwise support a means for determining a baseline blood pressure metric associated with the user. In some examples, the blood pressure difference component 770 may be configured as or otherwise support a means for determining a difference between the baseline blood pressure metric and the blood pressure metric. In some examples, the user interface manager 775 may be configured as or otherwise support a means for causing a GUI of a user device to display information associated with the difference between the baseline blood pressure metric and the blood pressure metric.

In some examples, the correlation coefficient component 780 may be configured as or otherwise support a means for determining a correlation coefficient between the first PPG waveform and the second PPG waveform based at least in part on the comparison of the first set of morphological features and the second set of morphological features, wherein the blood pressure metric is based at least in part on the correlation coefficient.

In some examples, to support acquiring the PPG data, the light emitting component 725 may be configured as or otherwise support a means for transmitting the first light and the second light using a light-emitting component of the wearable device. In some examples, to support acquiring the PPG data, the photodetector component 730 may be configured as or otherwise support a means for receiving the first light and the second light using a photodetector of the wearable device. In some examples, to support acquiring the PPG data, the PPG waveform component 7115 may be configured as or otherwise support a means for generating the first PPG waveform and the second PPG waveform based at least in part on receiving the first light and the second light, respectively, via the photodetector.

In some examples, the first wavelength comprises a first wavelength range associated with IR light. In some examples, the second wavelength comprises a second wavelength range associated with red light.

In some examples, the curvature component 785 may be configured as or otherwise support a means for determining a first curvature signal associated with a relative curvature of the first PPG waveform, and a second curvature signal associated with a relative curvature of the second PPG waveform. In some examples, the first peak component 790 may be configured as or otherwise support a means for determining a first peak of the first curvature signal corresponding to the first systolic peak of the first PPG waveform, wherein the first set of morphological features comprises a first timing of the first peak. In some examples, the second peak component 795 may be configured as or otherwise support a means for determining a second peak of the second curvature signal corresponding to the second systolic peak of the second PPG waveform, wherein the second set of morphological features comprises a second timing of the second peak. In some examples, the timing delay component 7100 may be configured as or otherwise support a means for determining a delay between the first timing of the first peak and the second timing of the second peak based at least in part on the comparison of the first and second sets of morphological features, wherein the blood pressure metric is based at least in part on the delay.

In some examples, the first curvature signal and the second curvature signal comprise second derivatives of the first PPG waveform and the second PPG waveform, respectively.

In some examples, the first wavelength comprises a first wavelength range associated with IR light, red light, or both. In some examples, the second wavelength comprises a second wavelength range associated with green light.

In some examples, the timing component 7105 may be configured as or otherwise support a means for determining a first timing of the first systolic peak of the first PPG waveform, and a second timing of the second systolic peak of the second PPG waveform, wherein the first set of morphological features and the second set of morphological features comprise the first timing and the second timing, respectively. In some examples, the timing delay component 7100 may be configured as or otherwise support a means for determining a delay between the first systolic peak of the first PPG waveform and the second systolic peak of the second PPG waveform based at least in part on the first timing and the second timing, wherein the blood pressure metric is based at least in part on the delay.

In some examples, the first wavelength comprises a first wavelength range associated with red light. In some examples, the second wavelength comprises a second wavelength range associated with green light.

In some examples, the PPG data is acquired during a time interval that a pressure between the wearable device and a tissue of the user is changed from a first pressure to a second pressure. In some examples, the first set of morphological features and the second set of morphological features comprise responses of the first PPG waveform and the second PPG waveform, respectively, to the change from the first pressure to the second pressure.

In some examples, the user interface manager 775 may be configured as or otherwise support a means for causing a GUI of a user device to display instructions for the user to selectively change the pressure from the first pressure to the second pressure during the time interval, wherein acquiring the PPG data throughout the time interval is based at least in part on the instructions.

In some examples, the physiological data acquisition manager 7110 may be configured as or otherwise support a means for acquiring physiological data from the user via the wearable device, the physiological data comprising at least the PPG data and acceleration data associated with movement of the user. In some examples, the blood pressure component 760 may be configured as or otherwise support a means for selectively adjusting the blood pressure metric based at least in part on the acceleration data.

In some examples, the wearable device comprises a wearable ring device.

In some examples, the first set of morphological features comprises a first amplitude of the first systolic peak, the first diastolic peak, or both. In some examples, the second set of morphological features comprises a second amplitude of the second systolic peak, the first diastolic peak, or both.

Figure 8:
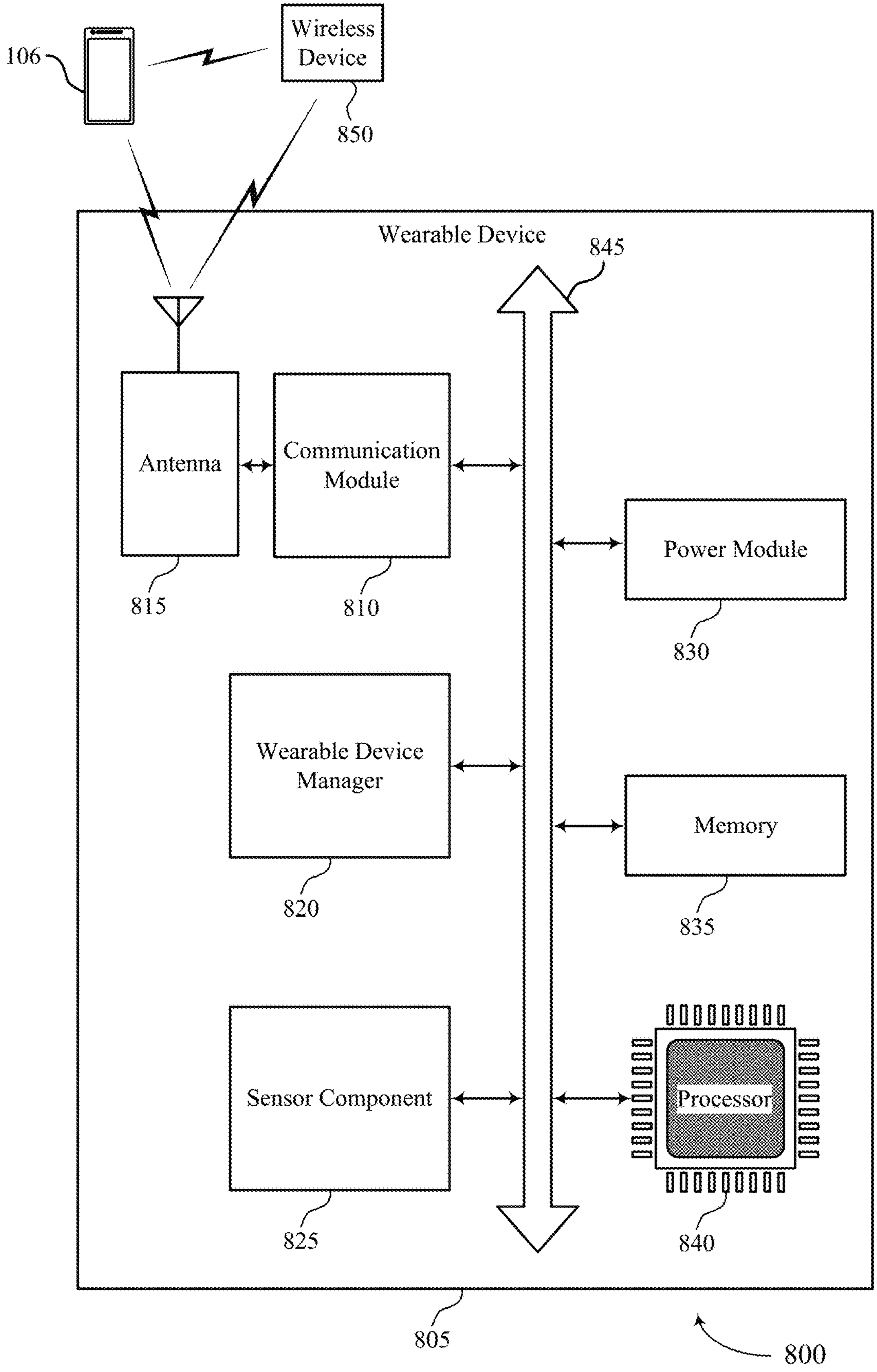
FIG. 8 illustrates a diagram of a system including a device that supports techniques for determining blood pressure based on morphological features of pulses in accordance with aspects of the present disclosure.

FIG. 8 illustrates a diagram of a system 800 including a device 805 that supports techniques for determining blood pressure based on morphological features of pulses in accordance with aspects of the present disclosure. The device 805 may be an example of or include the components of a device 605 as described herein. The device 805 may include an example of a wearable device 104, as described previously herein. The device 805 may include components for bi-directional communications including components for transmitting and receiving communications with a user device 106 and a server 110, such as a wearable device manager 820, a communication module 810, an antenna 815, a sensor component 825, a power module 830, a memory 835, a processor 840, and a wireless device 850. These components may be in electronic communication or otherwise coupled (e.g., operatively, communicatively, functionally, electronically, electrically) via one or more buses (e.g., a bus 845).

For example, the wearable device manager 820 may be configured as or otherwise support a means for one or more light-emitting components configured to emit light associated with at least a first wavelength and a second wavelength. The wearable device manager 820 may be configured as or otherwise support a means for one or more photodetectors configuring to receive light emitted by the one or more light-emitting components. The wearable device manager 820 may be configured as or otherwise support a means for a controller communicatively coupling to the one or more light-emitting components and the one or more photodetectors, the controller configured to. The wearable device manager 820 may be configured as or otherwise support a means for transmitting, during a time interval including a heartbeat of a user and using the one or more light-emitting components, first light associated with the first wavelength and second light associated with the second wavelength. The wearable device manager 820 may be configured as or otherwise support a means for acquiring PPG data from the user based at least in part on receiving the first light and the second light via the one or more photodetectors, the PPG data comprising at least a first PPG waveform acquired using the first light associated with the first wavelength and a second PPG waveform acquired using the second light associated with the second wavelength. The wearable device manager 820 may be configured as or otherwise support a means for determining a first set of morphological features associated with the first PPG waveform based at least in part on a first systolic peak and a first diastolic peak corresponding to the heartbeat within the first PPG waveform. The wearable device manager 820 may be configured as or otherwise support a means for determining a second set of morphological features associated with the second PPG waveform based at least in part on a second systolic peak and a second diastolic peak corresponding to the heartbeat within the second PPG waveform. The wearable device manager 820 may be configured as or otherwise support a means for determining a blood pressure metric for the user based at least in part on a comparison of the first set of morphological features and the second set of morphological features.

For example, the wearable device manager 820 may be configured as or otherwise support a means for acquiring PPG data from a user using a wearable device, the PPG data collected during a time interval including a heartbeat of the user, the PPG data comprising at least a first PPG waveform acquired using first light associated with a first wavelength and a second PPG waveform acquired using second light associated with a second wavelength. The wearable device manager 820 may be configured as or otherwise support a means for determining a first set of morphological features associated with the first PPG waveform based at least in part on a first systolic peak and a first diastolic peak corresponding to the heartbeat within the first PPG waveform. The wearable device manager 820 may be configured as or otherwise support a means for determining a second set of morphological features associated with the second PPG waveform based at least in part on a second systolic peak and a second diastolic peak corresponding to the heartbeat within the second PPG waveform. The wearable device manager 820 may be configured as or otherwise support a means for determining a blood pressure metric for the user based at least in part on a comparison of the first set of morphological features and the second set of morphological features.

By including or configuring the wearable device manager 820 in accordance with examples as described herein, the device 805 may support techniques for determining blood pressure based on morphological features of pulses. That is, the device 805 may improve user experience by communicating blood pressure metrics to the user on a timely basis without the need to visit a doctor for a blood pressure test.

It should be noted that the methods described above describe possible implementations, and that the operations and the steps may be rearranged or otherwise modified and that other implementations are possible. Furthermore, aspects from two or more of the methods may be combined.

A method is described. The method may include one or more light-emitting components configured to emit light associated with at least a first wavelength and a second wavelength, one or more photodetectors configured to receive light emitted by the one or more light-emitting components, a controller communicatively coupled to the one or more light-emitting components and the one or more photodetectors, the controller configured to, transmit, during a time interval including a heartbeat of a user and using the one or more light-emitting components, first light associated with the first wavelength and second light associated with the second wavelength, acquire PPG data from the user based at least in part on receiving the first light and the second light via the one or more photodetectors, the PPG data comprising at least a first PPG waveform acquired using the first light associated with the first wavelength and a second PPG waveform acquired using the second light associated with the second wavelength, determine a first set of morphological features associated with the first PPG waveform based at least in part on a first systolic peak and a first diastolic peak corresponding to the heartbeat within the first PPG waveform, determine a second set of morphological features associated with the second PPG waveform based at least in part on a second systolic peak and a second diastolic peak corresponding to the heartbeat within the second PPG waveform, and determine a blood pressure metric for the user based at least in part on a comparison of the first set of morphological features and the second set of morphological features.

An apparatus is described. The apparatus may include a processor, memory coupled with the processor, and instructions stored in the memory. The instructions may be executable by the processor to cause the apparatus to one or more light-emit components configured to emit light associated with at least a first wavelength and a second wavelength, one or more photodetectors configure to receive light emitted by the one or more light-emitting components, a controller communicatively couple to the one or more light-emitting components and the one or more photodetectors, the controller configured to, transmit, during a time interval including a heartbeat of a user and using the one or more light-emitting components, first light associated with the first wavelength and second light associated with the second wavelength, acquire PPG data from the user based at least in part on receiving the first light and the second light via the one or more photodetectors, the PPG data comprising at least a first PPG waveform acquired using the first light associated with the first wavelength and a second PPG waveform acquired using the second light associated with the second wavelength, determine a first set of morphological features associated with the first PPG waveform based at least in part on a first systolic peak and a first diastolic peak corresponding to the heartbeat within the first PPG waveform, determine a second set of morphological features associated with the second PPG waveform based at least in part on a second systolic peak and a second diastolic peak corresponding to the heartbeat within the second PPG waveform, and determine a blood pressure metric for the user based at least in part on a comparison of the first set of morphological features and the second set of morphological features.

Another apparatus is described. The apparatus may include means for one or more light-emitting components configured to emit light associated with at least a first wavelength and a second wavelength, means for one or more photodetectors configured to receive light emitted by the one or more light-emitting components, means for a controller communicatively coupled to the one or more light-emitting components and the one or more photodetectors, the controller configured to, means for transmit, during a time interval including a heartbeat of a user and using the one or more light-emitting components, first light associated with the first wavelength and second light associated with the second wavelength, means for acquire PPG data from the user based at least in part on receiving the first light and the second light via the one or more photodetectors, the PPG data comprising at least a first PPG waveform acquired using the first light associated with the first wavelength and a second PPG waveform acquired using the second light associated with the second wavelength, means for determine a first set of morphological features associated with the first PPG waveform based at least in part on a first systolic peak and a first diastolic peak corresponding to the heartbeat within the first PPG waveform, means for determine a second set of morphological features associated with the second PPG waveform based at least in part on a second systolic peak and a second diastolic peak corresponding to the heartbeat within the second PPG waveform, and means for determine a blood pressure metric for the user based at least in part on a comparison of the first set of morphological features and the second set of morphological features.

A non-transitory computer-readable medium storing code is described. The code may include instructions executable by a processor to one or more light-emit components configured to emit light associated with at least a first wavelength and a second wavelength, one or more photodetectors configure to receive light emitted by the one or more light-emitting components, a controller communicatively couple to the one or more light-emitting components and the one or more photodetectors, the controller configured to, transmit, during a time interval including a heartbeat of a user and using the one or more light-emitting components, first light associated with the first wavelength and second light associated with the second wavelength, acquire PPG data from the user based at least in part on receiving the first light and the second light via the one or more photodetectors, the PPG data comprising at least a first PPG waveform acquired using the first light associated with the first wavelength and a second PPG waveform acquired using the second light associated with the second wavelength, determine a first set of morphological features associated with the first PPG waveform based at least in part on a first systolic peak and a first diastolic peak corresponding to the heartbeat within the first PPG waveform, determine a second set of morphological features associated with the second PPG waveform based at least in part on a second systolic peak and a second diastolic peak corresponding to the heartbeat within the second PPG waveform, and determine a blood pressure metric for the user based at least in part on a comparison of the first set of morphological features and the second set of morphological features.

Some examples of the method, apparatuses, and non-transitory computer-readable medium described herein may further include operations, features, means, or instructions for determine a baseline blood pressure metric associated with the user, determine a difference between the baseline blood pressure metric and the blood pressure metric, and cause a GUI of a user device to display information associated with the difference between the baseline blood pressure metric and the blood pressure metric.

Some examples of the method, apparatuses, and non-transitory computer-readable medium described herein may further include operations, features, means, or instructions for determine a correlation coefficient between the first PPG waveform and the second PPG waveform based at least in part on the comparison of the first set of morphological features and the second set of morphological features, wherein the blood pressure metric may be based at least in part on the correlation coefficient.

In some examples of the method, apparatuses, and non-transitory computer-readable medium described herein, the first wavelength comprises a first wavelength range associated with IR light and the second wavelength comprises a second wavelength range associated with red light.

Some examples of the method, apparatuses, and non-transitory computer-readable medium described herein may further include operations, features, means, or instructions for determine a first curvature signal associated with a relative curvature of the first PPG waveform, and a second curvature signal associated with a relative curvature of the second PPG waveform, determine a first peak of the first curvature signal corresponding to the first systolic peak of the first PPG waveform, wherein the first set of morphological features comprises a first timing of the first peak, determine a second peak of the second curvature signal corresponding to the second systolic peak of the second PPG waveform, wherein the second set of morphological features comprises a second timing of the second peak, and determine a delay between the first timing of the first peak and the second timing of the second peak based at least in part on the comparison of the first and second sets of morphological features, wherein the blood pressure metric may be based at least in part on the delay.

In some examples of the method, apparatuses, and non-transitory computer-readable medium described herein, the first curvature signal and the second curvature signal comprise second derivatives of the first PPG waveform and the second PPG waveform, respectively.

In some examples of the method, apparatuses, and non-transitory computer-readable medium described herein, the first wavelength comprises a first wavelength range associated with IR light, red light, or both and the second wavelength comprises a second wavelength range associated with green light.

Some examples of the method, apparatuses, and non-transitory computer-readable medium described herein may further include operations, features, means, or instructions for determine a first timing of the first systolic peak of the first PPG waveform, and a second timing of the second systolic peak of the second PPG waveform, wherein the first set of morphological features and the second set of morphological features comprise the first timing and the second timing, respectively and determine a delay between the first systolic peak of the first PPG waveform and the second systolic peak of the second PPG waveform based at least in part on the first timing and the second timing, wherein the blood pressure metric may be based at least in part on the delay.

In some examples of the method, apparatuses, and non-transitory computer-readable medium described herein, the first wavelength comprises a first wavelength range associated with red light and the second wavelength comprises a second wavelength range associated with green light.

In some examples of the method, apparatuses, and non-transitory computer-readable medium described herein, the PPG data may be acquired during a time interval that a pressure between the wearable device and a tissue of the user may be changed from a first pressure to a second pressure and the first set of morphological features and the second set of morphological features comprise responses of the first PPG waveform and the second PPG waveform, respectively, to the change from the first pressure to the second pressure.

Some examples of the method, apparatuses, and non-transitory computer-readable medium described herein may further include operations, features, means, or instructions for cause a GUI of a user device to display instructions for the user to selectively change the pressure from the first pressure to the second pressure during the time interval, wherein acquiring the PPG data throughout the time interval may be based at least in part on the instructions.

Some examples of the method, apparatuses, and non-transitory computer-readable medium described herein may further include operations, features, means, or instructions for acquire physiological data from the user via the wearable device, the physiological data comprising at least the PPG data and acceleration data associated with movement of the user and selectively adjust the blood pressure metric based at least in part on the acceleration data.

In some examples of the method, apparatuses, and non-transitory computer-readable medium described herein, the wearable device comprises a wearable ring device.

In some examples of the method, apparatuses, and non-transitory computer-readable medium described herein, the first set of morphological features comprises a first amplitude of the first systolic peak, the first diastolic peak, or both and the second set of morphological features comprises a second amplitude of the second systolic peak, the first diastolic peak, or both.

A method is described. The method may include acquiring PPG data from a user using a wearable device, the PPG data collected during a time interval including a heartbeat of the user, the PPG data comprising at least a first PPG waveform acquired using first light associated with a first wavelength and a second PPG waveform acquired using second light associated with a second wavelength, determining a first set of morphological features associated with the first PPG waveform based at least in part on a first systolic peak and a first diastolic peak corresponding to the heartbeat within the first PPG waveform, determining a second set of morphological features associated with the second PPG waveform based at least in part on a second systolic peak and a second diastolic peak corresponding to the heartbeat within the second PPG waveform, and determining a blood pressure metric for the user based at least in part on a comparison of the first set of morphological features and the second set of morphological features.

An apparatus is described. The apparatus may include a processor, memory coupled with the processor, and instructions stored in the memory. The instructions may be executable by the processor to cause the apparatus to acquire PPG data from a user using a wearable device, the PPG data collected during a time interval including a heartbeat of the user, the PPG data comprising at least a first PPG waveform acquired using first light associated with a first wavelength and a second PPG waveform acquired using second light associated with a second wavelength, determine a first set of morphological features associated with the first PPG waveform based at least in part on a first systolic peak and a first diastolic peak corresponding to the heartbeat within the first PPG waveform, determine a second set of morphological features associated with the second PPG waveform based at least in part on a second systolic peak and a second diastolic peak corresponding to the heartbeat within the second PPG waveform, and determine a blood pressure metric for the user based at least in part on a comparison of the first set of morphological features and the second set of morphological features.

Another apparatus is described. The apparatus may include means for acquiring PPG data from a user using a wearable device, the PPG data collected during a time interval including a heartbeat of the user, the PPG data comprising at least a first PPG waveform acquired using first light associated with a first wavelength and a second PPG waveform acquired using second light associated with a second wavelength, means for determining a first set of morphological features associated with the first PPG waveform based at least in part on a first systolic peak and a first diastolic peak corresponding to the heartbeat within the first PPG waveform, means for determining a second set of morphological features associated with the second PPG waveform based at least in part on a second systolic peak and a second diastolic peak corresponding to the heartbeat within the second PPG waveform, and means for determining a blood pressure metric for the user based at least in part on a comparison of the first set of morphological features and the second set of morphological features.

A non-transitory computer-readable medium storing code is described. The code may include instructions executable by a processor to acquire PPG data from a user using a wearable device, the PPG data collected during a time interval including a heartbeat of the user, the PPG data comprising at least a first PPG waveform acquired using first light associated with a first wavelength and a second PPG waveform acquired using second light associated with a second wavelength, determine a first set of morphological features associated with the first PPG waveform based at least in part on a first systolic peak and a first diastolic peak corresponding to the heartbeat within the first PPG waveform, determine a second set of morphological features associated with the second PPG waveform based at least in part on a second systolic peak and a second diastolic peak corresponding to the heartbeat within the second PPG waveform, and determine a blood pressure metric for the user based at least in part on a comparison of the first set of morphological features and the second set of morphological features.

Some examples of the method, apparatuses, and non-transitory computer-readable medium described herein may further include operations, features, means, or instructions for determining a baseline blood pressure metric associated with the user, determining a difference between the baseline blood pressure metric and the blood pressure metric, and causing a GUI of a user device to display information associated with the difference between the baseline blood pressure metric and the blood pressure metric.

Some examples of the method, apparatuses, and non-transitory computer-readable medium described herein may further include operations, features, means, or instructions for determining a correlation coefficient between the first PPG waveform and the second PPG waveform based at least in part on the comparison of the first set of morphological features and the second set of morphological features, wherein the blood pressure metric may be based at least in part on the correlation coefficient.

In some examples of the method, apparatuses, and non-transitory computer-readable medium described herein, acquiring the PPG data may include operations, features, means, or instructions for transmitting the first light and the second light using a light-emitting component of the wearable device, receiving the first light and the second light using a photodetector of the wearable device, and generating the first PPG waveform and the second PPG waveform based at least in part on receiving the first light and the second light, respectively, via the photodetector.

In some examples of the method, apparatuses, and non-transitory computer-readable medium described herein, the first wavelength comprises a first wavelength range associated with IR light and the second wavelength comprises a second wavelength range associated with red light.

Some examples of the method, apparatuses, and non-transitory computer-readable medium described herein may further include operations, features, means, or instructions for determining a first curvature signal associated with a relative curvature of the first PPG waveform, and a second curvature signal associated with a relative curvature of the second PPG waveform, determining a first peak of the first curvature signal corresponding to the first systolic peak of the first PPG waveform, wherein the first set of morphological features comprises a first timing of the first peak, determining a second peak of the second curvature signal corresponding to the second systolic peak of the second PPG waveform, wherein the second set of morphological features comprises a second timing of the second peak, and determining a delay between the first timing of the first peak and the second timing of the second peak based at least in part on the comparison of the first and second sets of morphological features, wherein the blood pressure metric may be based at least in part on the delay.

In some examples of the method, apparatuses, and non-transitory computer-readable medium described herein, the first curvature signal and the second curvature signal comprise second derivatives of the first PPG waveform and the second PPG waveform, respectively.

In some examples of the method, apparatuses, and non-transitory computer-readable medium described herein, the first wavelength comprises a first wavelength range associated with IR light, red light, or both and the second wavelength comprises a second wavelength range associated with green light.

Some examples of the method, apparatuses, and non-transitory computer-readable medium described herein may further include operations, features, means, or instructions for determining a first timing of the first systolic peak of the first PPG waveform, and a second timing of the second systolic peak of the second PPG waveform, wherein the first set of morphological features and the second set of morphological features comprise the first timing and the second timing, respectively and determining a delay between the first systolic peak of the first PPG waveform and the second systolic peak of the second PPG waveform based at least in part on the first timing and the second timing, wherein the blood pressure metric may be based at least in part on the delay.

In some examples of the method, apparatuses, and non-transitory computer-readable medium described herein, the first wavelength comprises a first wavelength range associated with red light and the second wavelength comprises a second wavelength range associated with green light.

In some examples of the method, apparatuses, and non-transitory computer-readable medium described herein, the PPG data may be acquired during a time interval that a pressure between the wearable device and a tissue of the user may be changed from a first pressure to a second pressure and the first set of morphological features and the second set of morphological features comprise responses of the first PPG waveform and the second PPG waveform, respectively, to the change from the first pressure to the second pressure.

Some examples of the method, apparatuses, and non-transitory computer-readable medium described herein may further include operations, features, means, or instructions for causing a GUI of a user device to display instructions for the user to selectively change the pressure from the first pressure to the second pressure during the time interval, wherein acquiring the PPG data throughout the time interval may be based at least in part on the instructions.

Some examples of the method, apparatuses, and non-transitory computer-readable medium described herein may further include operations, features, means, or instructions for acquiring physiological data from the user via the wearable device, the physiological data comprising at least the PPG data and acceleration data associated with movement of the user and selectively adjusting the blood pressure metric based at least in part on the acceleration data.

In some examples of the method, apparatuses, and non-transitory computer-readable medium described herein, the wearable device comprises a wearable ring device.

In some examples of the method, apparatuses, and non-transitory computer-readable medium described herein, the first set of morphological features comprises a first amplitude of the first systolic peak, the first diastolic peak, or both and the second set of morphological features comprises a second amplitude of the second systolic peak, the first diastolic peak, or both.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as IR, radio, and microwave, then the coaxial cable, fiber optic cable, twisted pair, DSL, or wireless technologies such as IR, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system for measuring blood pressure, comprising:

a wearable device configured to acquire physiological data from a user, the wearable device comprising:

one or more light-emitting components configured to transmit, during a time interval including a heartbeat of the user, first light associated with a first wavelength and second light associated with a second wavelength, wherein the first light comprises infrared light having the first wavelength, and wherein the second light comprises red light having the second wavelength; and one or more photodetectors configured to receive the first light and the second light emitted by the one or more light-emitting components; and one or more processors communicatively coupled with the wearable device, the one or more processors configured to:

acquire photoplethysmogram (PPG) data from the user based at least in part on the first light and the second light received by the one or more photodetectors, the PPG data comprising at least a first PPG waveform acquired using the infrared light and a second PPG waveform acquired using the red light;

determine a first set of morphological features and a second set of morphological features associated with the first PPG waveform and the second PPG waveform, respectively;

compare the first set of morphological features and the second set of morphological features, the first set of morphological features comprising a peak of a second derivative of the first PPG waveform and the second set of the morphological features comprising a peak of a second derivative of the second PPG waveform;

determine a correlation coefficient between the first PPG waveform and the second PPG waveform based at least in part on a comparison between the peak of the second derivative of the first PPG waveform and the peak of the second derivative of the second PPG waveform; and determine a blood pressure metric for the user based at least in part on the correlation coefficient and the comparison of the peak of the second derivative of the first PPG waveform and the peak of the second derivative of the second PPG waveform.

2. The system of claim 1, wherein the one or more processors are further configured to:

perform a phase analysis between the first PPG waveform and the second PPG waveform over the time interval, wherein the correlation coefficient is based at least in part on the phase analysis; and determine a blood pressure category of the user based at least in part on the phase analysis and the correlation coefficient, wherein the blood pressure metric is based at least in part on the blood pressure category, and wherein the blood pressure category comprises one of a normotensive blood pressure, a prehypertensive blood pressure, or a hypertensive blood pressure.

3. The system of claim 1, wherein the one or more processors are further configured to:

acquire baseline PPG data from the user, the baseline PPG data comprising a plurality of baseline PPG pulses associated with a plurality of heartbeats of the user;

determine a set of baseline morphological features associated with the plurality of baseline PPG pulses;

generate one or more PPG profiles for the user based at least in part on the set of baseline morphological features; and compare the first PPG waveform and the second PPG waveform to the one or more PPG profiles, wherein determining the first and second sets of morphological features, determining the correlation coefficient, determining the blood pressure metric, or any combination thereof, is based at least in part on both the first PPG waveform and the second PPG waveform matching the one or more PPG profiles.

4. The system of claim 3, wherein the one or more PPG profiles comprise a plurality of morphological feature value ranges for a plurality of morphological features, wherein the first PPG waveform and the second PPG waveform match the one or more PPG profiles based at least in part on the first set of morphological features and the second set of morphological features falling within the plurality of morphological feature value ranges of the one or more PPG profiles.

5. The system of claim 3, wherein the one or more processors are further configured to:

determine a plurality of average values for a plurality of morphological features of the plurality of baseline PPG pulses based at least in part on the set of baseline morphological features, wherein the one or more PPG profiles are generated based at least in part on the plurality of average values.

6. The system of claim 3, wherein the first PPG waveform comprises a first set of PPG pulses, and wherein the second PPG waveform comprises a second set of PPG pulses, wherein the one or more processors are further configured to:

identify a first subset of PPG pulses within the first set of PPG pulses of the first PPG waveform that match the one or more PPG profiles, wherein the first set of morphological features are based at least in part on the first subset of PPG pulses; and identify a second subset of PPG pulses within the second set of PPG pulses of the second PPG waveform that match the one or more PPG profiles, wherein the second set of morphological features are based at least in part on the second subset of PPG pulses.

7. The system of claim 6, wherein the one or more processors are further configured to:

identify a third subset of PPG pulses within the first set of PPG pulses and the second set of PPG pulses that do not match the one or more PPG profiles, wherein the third subset of PPG pulses are excluded from the determination of the first set of morphological features and the second set of morphological features.

8. The system of claim 3, wherein the baseline PPG data is collected throughout a duration that the user is in a plurality of postures, the plurality of postures comprising a standing posture, a sitting posture, a lying down posture, or any combination thereof, wherein the one or more PPG profiles comprise a plurality of PPG profiles corresponding to the respective plurality of postures.

9. The system of claim 8, wherein the one or more processors are further configured to:

identify a posture of the user during the time interval, the posture comprising one of the plurality of postures; and compare the first PPG waveform and the second PPG waveform to a PPG profile of the plurality of PPG profiles that corresponds to the posture, wherein determining the first and second sets of morphological features, determining the correlation coefficient, determining the blood pressure metric, or any combination thereof, is based at least in part on both the first PPG waveform and the second PPG waveform matching the PPG profile that corresponds to the posture.

10. The system of claim 1, wherein the one or more processors are further configured to:

determine a posture of the user; and evaluate the first set of morphological features and the second set of morphological features based at least in part on the posture of the user, wherein the blood pressure metric is based at least in part on evaluating the first and second sets of morphological features.

11. The system of claim 1, wherein the one or more processors are further configured to:

determine a first timing of a first systolic peak of the heartbeat within the first PPG waveform, and a second timing of a second systolic peak of the heartbeat within the second PPG waveform, wherein the first set of morphological features and the second set of morphological features comprise the first timing and the second timing, respectively; and determine a delay between the first systolic peak of the first PPG waveform and the second systolic peak of the second PPG waveform based at least in part on the first timing and the second timing, wherein the blood pressure metric is based at least in part on the delay.

12. The system of claim 1, wherein the PPG data is acquired during a time interval that a pressure between the wearable device and a tissue of the user is changed from a first pressure to a second pressure, wherein the first set of morphological features and the second set of morphological features comprise responses of the first PPG waveform and the second PPG waveform, respectively, to the change from the first pressure to the second pressure.

13. The system of claim 1, wherein the one or more processors are further configured to:

acquire the physiological data from the user via the wearable device, the physiological data comprising at least the PPG data and acceleration data associated with movement of the user; and selectively adjust the blood pressure metric based at least in part on the acceleration data.

14. The system of claim 1, wherein the wearable device comprises a wearable ring device.

15. The system of claim 1, wherein the first set of morphological features comprises a first amplitude of a first systolic peak of the heartbeat within the first PPG waveform, a first diastolic peak of the heartbeat within the first PPG waveform, or both, and wherein the second set of morphological features comprises a second amplitude of a second systolic peak of the heartbeat within the second PPG waveform, a second diastolic peak of the heartbeat within the second PPG waveform, or both.

16. A method for measuring blood pressure comprising:

acquiring photoplethysmogram (PPG) data from a user using a wearable device, the PPG data collected during a time interval including a heartbeat of the user, the PPG data comprising at least a first PPG waveform acquired using infrared light and a second PPG waveform acquired using red light;

determining a first set of morphological features and a second set of morphological features associated with the first PPG waveform and the second PPG waveform, respectively;

comparing the first set of morphological features and the second set of morphological features, the first set of morphological features comprising a peak of a second derivative of the first PPG waveform and the second set of the morphological features comprising a peak of a second derivative of the second PPG waveform;

determining a correlation coefficient between the first PPG waveform and the second PPG waveform based at least in part on a comparison between the peak of the second derivative of the first PPG waveform and the peak of the second derivative of the second PPG waveform; and determining a blood pressure metric for the user based at least in part on the correlation coefficient and the comparison of the peak of the second derivative of the first PPG waveform and the peak of the second derivative of the second PPG waveform.

17. The method of claim 16, further comprising:

performing a phase analysis between the first PPG waveform and the second PPG waveform over the time interval, wherein the correlation coefficient is based at least in part on the phase analysis; and determining a blood pressure category of the user based at least in part on the phase analysis and the correlation coefficient, wherein the blood pressure metric is based at least in part on the blood pressure category, and wherein the blood pressure category comprises one of a normotensive blood pressure, a prehypertensive blood pressure, or a hypertensive blood pressure.

18. The method of claim 16, further comprising:

acquiring baseline PPG data from the user, the baseline PPG data comprising a plurality of baseline PPG pulses associated with a plurality of heartbeats of the user;

determining a set of baseline morphological features associated with the plurality of baseline PPG pulses;

generating one or more PPG profiles for the user based at least in part on the set of baseline morphological features; and comparing the first PPG waveform and the second PPG waveform to the one or more PPG profiles, wherein determining the first and second sets of morphological features, determining the correlation coefficient, determining the blood pressure metric, or any combination thereof, is based at least in part on both the first PPG waveform and the second PPG waveform matching the one or more PPG profiles.

* * * * *